(12) United States Patent
Leblanc et al.

(10) Patent No.: US 6,777,433 B2
(45) Date of Patent: Aug. 17, 2004

(54) PROTEIN TYROSINE PHOSPHATASE 1B (PTP-1B) INHIBITORS CONTAINING TWO ORTHO-SUBSTITUTED AROMATIC PHOSPHONATES

(75) Inventors: Yves Leblanc, Kirkland (CA); Claude Dufresne, Dollard Des Ormeaux (CA); Jacques Yves Gauthier, Laval (CA); Robert Young, Senneville (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 10/185,170

(22) Filed: Jun. 28, 2002

(65) Prior Publication Data

US 2003/0114703 A1 Jun. 19, 2003

Related U.S. Application Data

(63) Continuation-in-part of application No. 09/745,220, filed on Dec. 21, 2000, now Pat. No. 6,448,429.
(60) Provisional application No. 60/171,427, filed on Dec. 22, 1999.

(51) Int. Cl.$^7$ ..................... A61K 31/425; A61K 31/40; C07D 517/00; C07D 271/06; C07D 249/16
(52) U.S. Cl. ..................... 514/367; 548/113; 548/131; 548/159; 548/179; 548/252; 548/260; 514/375; 514/383; 514/394; 514/412; 514/414; 514/422
(58) Field of Search .................... 548/113, 159, 548/260, 179, 252, 131; 514/367, 375, 383, 394, 414, 422, 412

(56) References Cited

U.S. PATENT DOCUMENTS

| 6,066,715 A | 5/2000 | Desmarais et al. |
| 6,245,754 B1 | 6/2001 | Kozikowski et al. |
| 6,448,429 B1 * | 9/2002 | Leblanc et al. ............. 558/161 |

FOREIGN PATENT DOCUMENTS

| WO | WO 97/40017 | 10/1997 |
| WO | WO 98/20156 | 5/1998 |
| WO | WO 99/31066 | 4/1999 |
| WO | WO 99/47529 | 9/1999 |
| WO | WO 00/17211 | 3/2000 |

OTHER PUBLICATIONS

Ahmad, et al., J. Biol. Chem., vol. 270, pp. 20503–20508, 1995.
Bin, et al., Tetrahedron, vol. 52, No. 30, pp. 9963–9970.
Caplan, et al., Bioorganic & Medicinal Chem. Letters, vol. 8, No. 5, pp. 515–520.
Charbonneau, et al., Proc. Natl. Acad. Sci. USA, vol. 86, pp. 5252–5256, 1989.
Fishcer, et al., Science, vol. 253, pp. 401–406, 1991.
Goldstein, Receptor vol. 3, pp. 1–15, 1993.
Kotoris, et al., J. Org. Chem., vol. 63, pp. 8052–8057, 1998.
Seely, et al., Diabetes, vol. 45, pp. 1379–1385, 1996.
Taylor, et al., Bioorg. Med. Chem., vol. 6(9), pp. 1457–1468, 1998.
Taylor, et al., Bioorg. Med. Chem., vol. 6, p. 2235, 1998.
Taylor, et al., Tetrahedron Letters, vol. 8, No. 45, pp. 8089–8092, 1996.
Taylor, et al., Tetrahedron, No. 54, pp. 1691–1714, 1998.
Wang, et al., Bioorg. Med. Chem., Let., vol. 8(4), pp. 345–350, 1998.
White, et al., J. Biol. Chem., vol. 269, pp. 1–4, 1994.
Yokomatsu, et al., Tetrahedron, vol. 54, No. 32, pp. 9341–9356.
Burke, et al., Bioorg. Med. Chem. Letters, vol. 9, pp. 347–352, 1999.
Yao, et al., Tetrahedron, vol. 55, pp. 2865–2874, 1999.
Beaulieu, et al.., J. Med. Chem., vol. 42, pp. 1757–1766, 1999.
Kotoris, et al., Bioorg. Med. Chem., vol. 8, pp. 3275–3280, 1998.
Taing, M.—Biochemistry, vol. 38, No. 12, pp. 3793–3803, 1999.
Charifson, et al., Biochemistry, US, American Chemical Society, 1997, pp. 6283–6293, vol. 36–No. 21.
Desmarais, S., et al., Biochemical Journal, 1999, pp. 219–223, vol. 337–No. 2.
Ye, et al—CA: 125:221958, ABS of Tetrahedron, pp. 9963–9970, 1996.
Blackburn, et al—CA: 128:265749, AS of Bioorganic Med Chem Lett, vol. 8 (5), pp. 515–520, 1998.

* cited by examiner

*Primary Examiner*—D. Margaret Seaman
(74) *Attorney, Agent, or Firm*—James L. McGinnis; Melvin Winokur

(57) ABSTRACT

The invention encompasses the novel class of compounds represented by formula I, which are inhibitors of the PTP-1B enzyme.

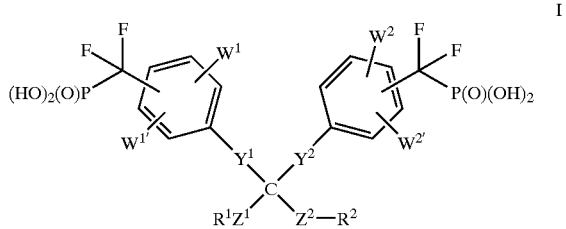

The invention also encompasses pharmaceutical compositions and methods of treating or preventing PTP-1B mediated diseases, including diabetes, obesity, and diabetes-related diseases.

21 Claims, No Drawings

PROTEIN TYROSINE PHOSPHATASE 1B (PTP-1B) INHIBITORS CONTAINING TWO ORTHO-SUBSTITUTED AROMATIC PHOSPHONATES

CROSS REFERENCE TO RELATED APPLICATIONS

This application is a Continuation-in-Part of U.S. application Ser. No. 09/745,220, now allowed, which was filed on Dec. 21, 2000, now U.S. Pat. No. 6,448,429, and which is based on and claims priority from U.S. Provisional Application No. 60/171,427, which was filed on Dec. 22, 1999. Commonly assigned U.S. application Ser. No. 09/398,356, filed on Sep. 17, 1999, now U.S. Pat. No. 6,174,874, and commonly assigned U.S. application Ser. Nos. 09/745,199, 09/745,211 and 09/745,222, all filed on Dec. 21, 2000, contain related subject matter.

BACKGROUND OF THE INVENTION

This invention relates to a novel class of phosphonic acid derivatives that are inhibitors of PTP-1B.

Protein tyrosine phosphatases are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 ("Seely") studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Recently, Kennedy et al., 1999, Science 283: 1544–1548 showed that protein tyrosine phosphatase PTP-1B is a negative regulator of the insulin signalling pathway, suggesting that inhibitors of this enzyme may be beneficial in the treatment of Type 2 diabetes. Mice lacking PTP-1B are resistant to both diabetes and obesity.

Thus, inhibitors of PTP-1B improve insulin-sensitivity. They have utility in controlling or treating Type 1 and Type 2 diabetes, in improving glucose tolerance, and in improving insulin sensitivity in patients in need thereof. The compounds may also be useful in treating or preventing cancer, neurodegenerative diseases and the like.

SUMMARY OF THE INVENTION

Compounds represented by formula I, including pharmaceutically acceptable salts thereof, and prodrugs thereof, are PTP-1B inhibitors that are useful in the treatment of diabetes and related medical conditions.

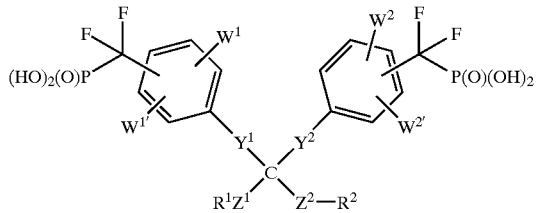

In Formula I, $R^1$ and $R^2$ are selected from the group consisting of: $C_{1-10}$alkyl$(R^a)_{0-7}$, $C_{2-10}$alkenyl$(R^a)_{0-7}$, Aryl$(R^a)_{0-3}$ and Het$(R^a)_{0-3}$;

wherein, each $R^a$ independently represents a member selected from the group consisting of: Aryl, OH, halogen, CN, $CO_2H$, $CO_2C_{1-6}$alkyl, $CO_2C_{2-6}$alkenyl, $OC_{1-10}$alkyl, $C(O)C_{1-6}$alkyl, $S(O)_yC_{1-6}$alkyl, $C_{1-6}$alkyl, $C_{1-6}$haloalkyl, $S(O)_yNR^{3'}R^{4'}$, wherein y is 0, 1, or 2, $C(O)NR^{3'}R^{4'}$, $NR^{3'}R^{4'}$, and Het, wherein each alkyl group in $R^a$ is optionally substituted with 1-7 groups independently selected from halogen, $OC_{1-3}$ alkyl, $CO_2H$, and $CO_2C_{1-3}$alkyl, and each Het and Aryl in $R^a$ is optionally substituted with 1–3 groups independently selected from $C_{1-3}$alkyl, halogen, $OC_{1-3}$ alkyl, $CO_2H$, and $CO_2C_{1-3}$alkyl;

Aryl is a 6–14 membered carbocyclic aromatic ring system comprising 1–3 phenyl rings, wherein rings are fused together so that adjacent rings share a common side when there is more than one aromatic ring;

Het represents a 5–10 membered aromatic ring system comprising one ring or two fused rings, 1–4 heteroatoms, 0–4 of which are N atoms and 0–2 of which are O or $S(O)_y$ wherein y is 0–2, and 0–2 carbonyl groups;

$Y^1$, $Y^2$, $Z^1$, and $Z^2$ each independently represents $—(CR^3R^4)_a—X—(CR^3R^4)_b—$ wherein a and b are integers 0–2 such that the sum of a and b equals 0, 1, 2, or 3;

X represents a bond, O, $S(O)_y$, $NR^{3'}$, $C(O)$, $OC(O)$, $C(O)O$, $C(O)NR^{3'}$, $NR^{3'}C(O)$ or $—CH=CH—$, where y is as previously defined;

$R^3$ and $R^4$ are each independently H, halogen, $C_{1-10}$alkyl or $C_{1-10}$haloalkyl;

$R^{3'}$ and $R^{4'}$ are each independently selected from the group consisting of: H, $C_{1-6}$alkyl, $C_{1-6}$haloalkyl, OH, $C(O)C_{1-6}$ alkyl, $C(O)Aryl$, $C(O)Het$, $C(O)C_{1-6}$ haloalkyl, Aryl and Het;

$W^1$ and $W^2$ are each in a position on the aromatic ring of Formula I adjacent to the $—CF_2P(O)(OH)_2$ substituent and are each independently selected from the group consisting of: OH, CN, halo, $OC_{1-6}alkyl(R^a)_{0-7}$, $S(O)_y C_{1-6}alkyl(R^a)_{0-7}$, with y equal to 0–2, $S(O)_3H$, $C_{1-6}alkyl(R^a)_{0-7}$, $CO_2H$, $CO_2C_{1-6}alkyl(R^a)_{0-7}$, $CO_2C_{2-6}$ alkenyl$(R^a)_{0-7}$, $C(O)C_{1-6}alkyl(R^a)_{0-7}$, $C(O)NR^{3'}R^{4'}$, $S(O)_yNR^{3'}R^{4'}$, $NR^{3'}R^{4'}$, Aryl, and Het, wherein $R^{3'}$ and $R^{4'}$ are as defined above; and $W^{1'}$ and $W^{2'}$ are optionally present on any remaining position on the aromatic ring and are each independently selected from H and from the same groups as $W^1$ and $W^2$.

Methods of treating and controlling diabetes, obesity, and other diseases and conditions using the compounds of Formula I are taught herein. Pharmaceutical compositions and combination treatments are also disclosed herein.

DETAILED DESCRIPTION OF THE INVENTION

In one subset of compounds, $W^{1'}$ and $W^{2'}$ are each independently selected from the group consisting of:
(a) hydrogen,
(b) halogen,
(c) $OC_{1-6}alkyl(R^a)_{0-7}$,
(d) $SC_{1-6}alkyl(R^a)_{0-7}$,
(e) $C_{1-6}alkyl(R^a)_{0-7}$,
(f) $CO_2H$,
(g) $CO_2—C_{1-6}alkyl(R^a)_{0-7}$,
(h) OH,
(i) $N(R^{3'})(R^{4'})$ and
(j) $C(O)C_{1-6}alkyl(R^a)_{0-7}$, and $W^1$ and $W^2$ are each independently selected from the group consisting of:
(a) halogen,
(b) $OC_{1-6}alkyl(R^a)_{0-7}$,
(c) $SC_{1-6}alkyl(R^a)_{0-7}$,
(d) $C_{1-6}alkyl(R^a)_{0-7}$,
(e) $CO_2H$,
(f) $CO_2—C_{1-6}alkyl(R^a)_{0-7}$,
(g) OH,
(h) $N(R^{3'})(R^{4'})$ and
(i) $C(O)C_{1-6}alkyl(R^a)_{0-7}$, and In a subset of the compounds described above, each $W^{1'}$ and $W^{2'}$ represents H, and $W^1$ and $W^2$ each independently represents a halogen, $C_{1-3}$ alkyl, $C_{1-3}$ fluoroalkyl, $OC_{1-3}$alkyl or $OC_{1-3}$ fluoroalkyl.

In a more specific subset of the above groups of compounds $W^1$ and $W^2$ each represents Br.

In another group of compounds, $Y^1$, $Y^2$, $Z^1$ and $Z^2$ are each independently selected from the group consisting of:
(a) —$CH_2$—,
(b) —O—$CH_2$—,
(c) —$C_2$—O—,
(d) —$CH_2$—O—$CH_2$—,
(e) —S—$CH_2$—,
(f) —$CH_2$—S—,
(g) —$CH_2$—S—$CH_2$—,
(h) —$S(O)_2$—$CH_2$—,
(i) —$CH_2$—$S(O)_2$—,
(j) —$CH_2$—$S(O)_2$—$CH_2$—,
(k) —$S(O)_2$—,
(l) —S—,
(m) —O—,
(n) —$NR^{3'}$,
(o) C(O), and
(p) a direct bond.

In another embodiment of the invention, $Y^1$, $Y^2$, $Z^1$ and $Z^2$ are each independently selected from the group consisting of: (a) —$CH_2$—, (b) —O—$CH_2$—, (c) —$CH_2$—O—, (d) —$CH_2$—O—$CH_2$—, (e) —S—$CH_2$—, (f) —$CH_2$—S— and (g) —$CH_2$—S—$CH_2$—.

In a more specific embodiment of the invention, as described above, $Y^1$, $Y^2$, $Z^1$, and $Z^2$ are each independently selected from the group consisting of C(O), $CH_2$, and a direct bond.

In another subset of compounds, $Z^1$ is a direct bond, $Z^2$ is C(O), and $Y^1$ and $Y^2$ are each $CH_2$.

In another embodiment of the invention as described above, $R^1$ and $R^2$ of Formula I are each independently selected from the group consisting of:
(a) $C_1$–$C_{10}$alkyl,
(b) $C_1$–$C_{10}$fluoroalkyl,
(c) unsubstituted, mono-, di- or tri-substituted phenyl wherein the optional substituents are selected from the group consisting of:
  (1) halo,
  (2) $C_{1-10}$alkoxy,
  (3) $C_{1-6}$alkylthio,
  (4) $CF_3$,
  (5) $C_{1-6}$alkyl,
  (6) —$CO_2H$
  (7) —$CO_2$—$C_{1-4}$alkyl,
  (8) unsubstituted, mono-, di-, or tri-substituted heteroaryl as defined in (d) below, wherein the optional substituents are selected from the groups in (c)(1)–(7) of this paragraph; and
  (9) unsubstituted, mono, di, or trisubstituted phenyl, wherein the optional substituents are selected from the groups in (c)(1)–(7) of this paragraph;
(d) unsubstituted, mono-, di- or tri-substituted heteroaryl, wherein the optional substituents are selected from the group consisting of:
  (1) halo,
  (2) $C_{1-10}$alkoxy,
  (3) $C_{1-6}$alkylthio,
  (4) $CF_3$,
  (5) $C_{1-6}$alkyl,
  (6) —$CO_2H$,
  (7) —$CO_2$—$C_{1-4}$alkyl,
  (8) unsubstituted, mono-, di-, or tri-substituted phenyl, wherein the optional substituents are selected from the groups in (d)(1)–(7) of this paragraph; and
  (9) unsubstituted, mono-, di-, or tri-substituted heteroaryl, wherein the optional substituents are selected from the groups in (d)(1)–(7) of this paragraph; and
(e) benzoheteroaryl, which includes the benzo fused analogs of Het.

In other embodiments of the above invention, $R^1$ and $R^2$ are each independently selected from the group consisting of phenyl and heteroaryl, wherein each phenyl and heteroaryl is optionally substituted with 1–3 $R^a$ substituents. In more preferred compounds, the substituents on $R^1$ and $R^2$, where $R^1$ and $R^2$ are phenyl, are independently selected from $C_{1-3}$ alkyl, $C_{1-3}$ fluoroalkyl and halogen.

In other subsets of compounds described above, $R^1$ and $R^2$ are each phenyl.

In other subsets of compounds, $W^{1'}$ and $W^{2'}$ are each H and $W^1$ and $W^2$ are each Br.

Finally, specific embodiments of compounds in accordance with Formula I are provided. These include the compounds shown in Table 1, Table 2 and Table 3; Compounds disclosed in the Methods of Synthesis; and the compound synthesized in Example 1, including prodrugs and pharmaceutically acceptable salts. The compound of Example 1 is named below: [2-bromo-4-(2-{3-bromo-4-[difluoro(phosphono)methyl]benzyl}-3-oxo-2,3-diphenylpropyl)phenyl](difluoro)methylphosphonic acid.

Methods of treating, preventing, or controlling diabetes and other diseases using the compounds of Formula I are disclosed herein. A method of treating, controlling or preventing diabetes and complications thereof in a mammalian patient in need of such treatment includes the administration to the patient of an anti-diabetic effective amount of a compound of Formula I. A method of treating, controlling or preventing obesity in a mammalian patient in need of such treatment comprises the administration to the patient an anti-obesity effective amount of a compound in accordance with claim 1. Such methods also include the administration of a second compound, which may be an anti-diabetic compound, an anti-obesity compound, or an HMG-CoA reductase inhibitor, in an amount effective to treat, control or prevent diabetes or obesity, or to improve a poor lipid profile.

A method of treating, controlling or preventing atherosclerosis in a mammalian patient in need of such treatment comprises administering to the patient an effective amount of a compound of Formula I and an effective amount of an HMG-CoA reductase inhibitor.

More generally, compounds of Formula I may be used as the active compound in a method for treating, preventing, or controlling one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease. The method comprises the administration of an effective amount of the compound of Formula I. Combination treatments can also be used, in which case the method comprises the administration of a compound of Formula I and an effective amount of one or more pharmaceutically active compounds selected from the group consisting of an HMG-CoA reductase inhibitor, an anti-obesity agent, and an antidiabetic compound.

Pharmaceutical compositions also can be made using the compounds of Formula I. Compositions that are suitable for the treatment, prevention or control of one or more diseases or conditions selected from Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease contain an effective amount of a compound of Formula I in combination with a pharmaceutically acceptable carrier.

Such pharmaceutical compositions may also include a second anti-diabetic agent or an anti-obesity agent. They may also include a cholesterol lowering agent. Pharmaceutical compositions may therefore include: (1) an effective amount of a compound of Formula I, (2) an effective amount of one or more pharmaceutically active compounds selected from the group consisting of an HMG-CoA reductase inhibitor, an anti-obesity agent, and an anti-diabetic agent, and (3) a pharmaceutically acceptable carrier.

Pharmaceutical compositions that contain a second active compound or composition and that are suitable for the treatment, prevention or control of one or more diseases or conditions selected from the group consisting of Type 1 diabetes, Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, adipose cell tumors, adipose cell carcinoma, liposarcoma, dyslipidemia, cancer, and neurodegenerative disease, may be comprised of the following:

(1) an effective amount of a compound of Formula 1;
(2) an effective amount of one or more pharmaceutically active compounds listed below; and
(3) a pharmaceutically acceptable carrier; where the pharmaceutically active compounds are selected from the group consisting of:
  (a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;
  (b) insulin or insulin mimetics;
  (c) sulfonylureas such as tolbutamide and glipizide, or related materials;
  (d) α-glucosidase inhibitors (such as acarbose);
  (e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) inhibitors of cholesterol absorption including beta-sitosterol and acyl CoA:cholesterol acyltransferase inhibitors including melinamide, and (vi) probucol;
  (f) PPARα/γ agonists;
  (g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $β_3$ adrenergic receptor agonists, and PPARγ antagonists and partial agonists;
  (h) ileal bile acid transporter inhibitors; and
  (i) insulin receptor activators.

---

Abbreviations
The following abbreviations have the indicated meanings:

| | |
|---|---|
| Ac = | acetyl |
| AIBN = | 2.2-azobisisobutyronitrile |
| DAST = | diethylamino sulfur trifluoride |
| DMF = | N,N-dimethylformamide |
| DMSO = | dimethyl sulfoxide |
| $Et_3N$ = | triethylamine |
| HBSS = | Hanks balanced salt solution |
| HEPES = | $N^1$-[2-Hydroxyethyl]piperazine-$N^4$-[2-ethanesulfonic acid] |
| KHMDS = | potassium hexamethyldisilazide |
| LDA = | lithium diisopropylamide |
| LHMDS = | lithium hexamethyldisilazide |
| NBS = | N-bromosuccinimide |
| nBuLi = | n-butyl lithium |

| Abbreviations |  |
|---|---|
| The following abbreviations have the indicated meanings: | |
| tBuLi = | t-Butyl lithium |
| Oxone ® = | potassium peroxymonosulfate |
| PTP = | protein tyrosine phosphatase |
| r.t. = | room temperature |
| rac. = | racemic |
| Tf = | trifluoromethanesulfonyl = triflyl |
| TFA = | trifluoroacetic acid |
| TFAA = | trifluoroacetic anhydride |
| TfO = | trifluoromethanesulfonate = triflate |
| THF = | tetrahydrofuran |
| TLC = | thin layer chromatography |
| Tz = | 1H (or 2H)-tetrazol-5-yl |

| Alkyl group abbreviations | |
|---|---|
| Me = | methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

| Dose Abbreviations | |
|---|---|
| bid = | bis in die = twice daily |
| qid = | quater in die = four times a day |
| tid = | ter in die = three times a day |

Alkyl means linear, branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0]decyl and the like.

Fluoroalkyl means alkyl groups of the indicated number of carbon atoms in which one or more hydrogens is replaced by fluorine. Examples are —CF$_3$, —CH$_2$CH$_2$F, —CH$_2$CF$_3$, c-Pr—F$_5$, c-Hex-F$_{11}$ and the like. Haloalkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl, 2-pentenyl, 2-cyclopentenyl, 3-cyclopentenyl, 2-methyl-cyclohexenyl, 2-cyclohexenyl, 3-cyclohexenyl and the like. Alkadienyl means the diunsaturated counterpart to alkenyl.

Alkynyl means linear, branched and cyclic structures, and combinations thereof containing a triple bond with the indicated number of carbon atoms. Examples of alkynyl groups include propargyl, 2-butynyl, 3-butynyl, 2-pentynyl, cyclopropylethynyl, and the like.

Alkylene, alkenylene, alkynylene, fluoroalkylene, alkadienylene, and the like, where the suffix "ene" has been added to the name of the monovalent radicals alkyl, alkenyl, alkynyl, fluoroalkyl, alkadienyl, and the like, describe divalent radicals that are the same as their monovalent counterparts, except that two hydrogen atoms rather than one are removed so that the radical will have two attachments.

Aryl means a 6–14 membered carbocyclic aromatic ring system comprising 1–3 phenyl rings. If two or more aromatic rings are present, then the rings are fused together, so that adjacent rings share a common side.

Heteroaryl (Het) as used herein represents a 5–10 membered aromatic ring system containing one ring or two fused rings, 1–4 heteroatoms, 0–4 of which are N atoms and 0–2 of which are O or S(O)$_y$ wherein y is as previously defined, and 0–2 carbonyl groups. Carbonyl groups, when present, are not counted as heteroatoms. Het includes, but is not limited to, furanyl, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone, 4-pyrone, pyrrolopyridine, furopyridine and thienopyridine.

Benzoheteroaryl, which is a subset of Het includes aromatic ring systems containing one or more heteroatoms which also have a fused 6-membered benzene ring, such as 2H-1-benzopyran-2-one, 4H-1-benzopyran-4-one, 2(3H)benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, and isoquinoline.

Another subset of heteroaryls includes 5-membered heteroaryls, such as the following:

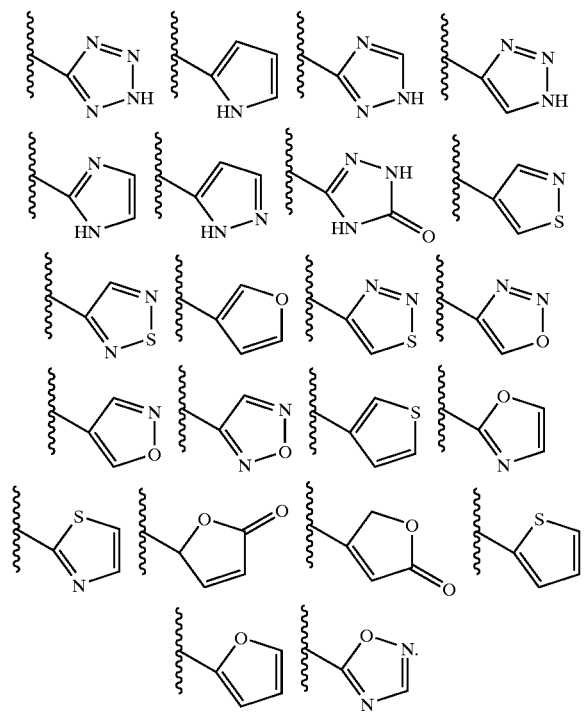

Preferred groups Het include tetrazole, oxadiazole, benzotriazole, benzothiazole, and indole.

When a heteroaromatic ring is specified as optionally having one or more heteroatoms, this means that at least one heteroatom is present, selected from O, S and N, and up to 4 such heteroatoms may be present, depending upon the size of the ring specified.

When a moiety is specified as being optionally substituted, then the same moiety may also remain unsubstituted, unless otherwise stated.

Finally, when a list of possible choices is provided for a given moiety, and the moiety is used in more than one position in a chemical formula, the selection of a choice for the moiety in each position is independent of other selections, unless the definition says otherwise.

Metabolites—Prodrugs

Metabolites of the compounds of this invention that are therapeutically active and that are described by formula I also are within the scope of the claimed invention, as are prodrugs, which are compounds that are converted to the claimed compounds or salts of the claimed compounds after they have been administered to a patient. A non-limiting example of a prodrug of the phosphonic acids of this invention would be a monoester or diester of one or more phosphonic acid groups, where the ester functionality has a structure that makes it easily hydrolyzed or metabolized after administration to a patient. Examples of such prodrugs are the compounds shown below, where R'=H or a $C_{1-6}$ alkyl group, and R"=a $C_{1-6}$ alkyl group or —$OC_{1-6}$ alkyl group, where Q is the residue of the molecule that is attached to the —$CF_2PO_3H_2$ group in formula I. The alkyl groups and alkoxy groups may optionally be substituted with one or more substituents independently selected from 1–5 halogen atoms, a phenyl group, or a mixture of these. The phenyl group, if present, may optionally be substituted with 1–3 substituents independently selected from halogen, —$CH_3$, —$CF_3$, —$OCH_3$ and —$OCF_3$. In these compounds, and as defined in general throughout this application, the alkyl groups and the alkyl portions of Oalkyl groups may be linear or branched and may optionally be cycloalkyl or may include a cycloalkyl group in their structure. For examples of related prodrug structures, see D. N. Srinivasta et al., Bioorganic Chemistry 12, 118–129 (1984).

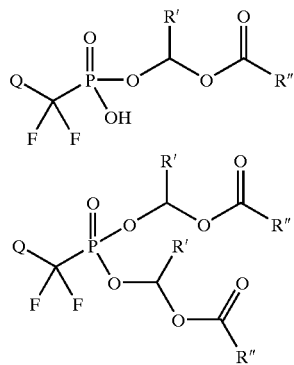

Other ester functionalities that may be used in the monoester or diester phosphonate prodrugs include phenyl esters and benzyl esters, where the phenyl ester groups have the structure-Ophenyl, and the benzyl ester groups have the structure —OCHR'phenyl, in which R' is H or $C_{1-6}$alkyl, and $C_{1-6}$alkyl is substituted as described above. In either case, phenyl is substituted as described above.

The prodrugs of this invention may therefore be defined as compounds having the formula Ia shown below:

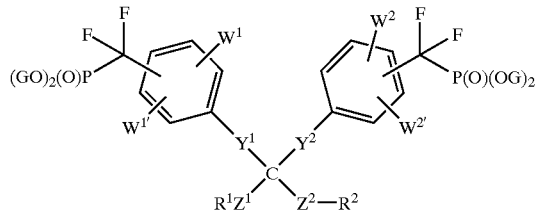

Ia

In the compound having Formula Ia, three groups G are independently selected from H, phenyl, —CHR'phenyl, and —CHR'OC(=O)R", and the fourth group G is selected from phenyl, —CHR'phenyl and —CHR'OC(=O)R", wherein each group R' is H or $C_{1-6}$alkyl and each group R" is —$C_{1-6}$alkyl or —$OC_{1-6}$alkyl, where $C_{1-6}$alkyl and the alkyl portion of —$OC_{1-6}$alkyl may optionally be substituted with one or more substituents independently selected from 1–5 halogen atoms, a phenyl group, or a mixture of these. The phenyl group in —CHR'phenyl, the phenyl group that is an optional substituent on $C_{1-6}$alkyl and —$OC_{1-6}$alkyl, and the phenyl ester group that is obtained when G is phenyl may optionally be substituted with 1–3 groups independently selected from halogen, —$CH_3$, —$CF_3$, —$OCH_3$ and —$OCF_3$. By this definition, one of the phosphonic acid groups is a monoester or diester and the other phosphonic acid group is a free acid or a monoester or diester.

In preferred compounds, the groups G that are not H are all the same because of the difficulty of synthesizing different G groups on the same phosphonates. In many cases, the prodrug will be a mixture of compounds having different levels of esterification on the phosphonic acid groups because of the difficulty of synthesizing a discrete pure compound.

Optical Isomers—Diastereomers—Geometric Isomers

Some of the compounds described herein contain one or more asymmetric centers and may thus give rise to diastereomers and enantiomers, which in turn can be resolved as optical isomers. The present invention includes all such diastereomers and enantiomers, including racemic mixtures and resolved, enantiomerically pure forms, and pharmaceutically acceptable salts thereof. Some of the compounds described herein contain olefinic double bonds, and unless specified otherwise, include both E and Z geometric isomers.

Salts

The pharmaceutical compositions of the present invention comprise a compound of the current invention as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment or of specific compounds which follows, references to the compounds of Formula I and other formulae are meant to include the pharmaceutically acceptable salts.

Utilities

Inhibitors of PTP-1B improve insulin-sensitivity and thus have utility in preventing or treating Type 1 and Type 2 diabetes, improving glucose tolerance and insulin-sensitivity when there is insulin-resistance, and in treating or preventing obesity, all in mammals that are in need of such treatments or that might benefit from such treatments. The compounds also exhibit a beneficial reduction in triglycerides and lipids. Compounds in the present class of phosphonic acids are advantageous over known phosphonic acids previously investigated as candidate PTP-1B inhibitors. The compounds of this invention are more potent inhibitors of PTP 1B when compared with known phosphonates. These compounds are active in intact cell-based assays.

The PTP-1B inhibitors may also be useful in the treatment, prevention or control of a number of conditions that accompany type 2 diabetes, including hyperlipidemia, hypertriglyceridemia, hypercholesterolemia (including beneficially raising low HDL levels), atherosclerosis, vascular restenosis, pancreatitis, adipose cell tumors, adipose cell carcinomas such as liposarcoma, dyslipidemia, inflammatory bowel disease, inflammation in general, and other disorders where insulin resistance is a component. Finally, the compounds may be used to treat or prevent cancer, such as prostate cancer, neurodegenerative diseases and the like.

Pharmaceutical Compositions

For the treatment of any of these PTP-1B-mediated diseases the active compound may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable nonirritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives, emollients and the like.

The pharmaceutical composition may also be further comprised of a second anti-diabetic or anti-obesity effective compound.

Dose Ranges

Dosage levels on the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B mediated diseases as defined above comprising an effective amount of the active compound and one or more other pharmaceutically active compounds, such as anti-diabetic compounds (for example, insulin, sulfonyl ureas, PPAR-alpha and/or -gamma ligands, including ligands that have both PPAR-alpha and -gamma activity), anti-obesity compounds, and compounds that improve the lipid profile of the patient.

Thus, the methods of treatment or prevention described herein may further be comprised of administering to said patient a second anti-diabetic compound in an amount effective to treat, control, or prevent diabetes, alone or in combination with the PTP-1B inhibitors of this invention.

Similarly, the methods of treatment or prevention described herein may further be comprised of administering to said patient an anti-obesity compound in an amount effective to treat, control or prevent obesity, alone or in combination with the PTP-1B inhibitors of this invention.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Examples of other pharmaceutically active compounds that may be combined with a compound of Formula I and administered in combination with the PTP-1B inhibitors include, but are not limited to, the following compounds or compositions or groups of compounds or compositions that are used as anti-diabetes compounds (a, b, c, d, f, and i below), anti-obesity compounds (g below), and/or compounds or compositions for lipid profile control (e and h below):

(a) insulin sensitizers including (i) PPARγ agonists such as the glitazones (e.g. troglitazone, pioglitazone, englitazone, MCC-555, rosiglitazone, and the like), and compounds disclosed in WO97/27857, 97/28115, 97/28137 and 97/27847; (ii) biguanides such as metformin and phenformin;

(b) insulin or insulin mimetics;

(c) sulfonylureas such as tolbutamide and glipizide, or related materials;

(d) α-glucosidase inhibitors (such as acarbose);

(e) cholesterol lowering agents such as (i) HMG-CoA reductase inhibitors (lovastatin, simvastatin and pravastatin, fluvastatin, atorvastatin, rivastatin and other statins), (ii) sequestrants (cholestyramine, colestipol and a dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and benzafibrate), (v) inhibitors of cholesterol absorption for example beta-sitosterol and (acyl CoA:cholesterol acyltransferase) inhibitors for example melinamide and (vi) probucol;

(f) PPARα/γ agonists;

(g) antiobesity compounds such as appetite suppressants, fenfluramine, dexfenfluramine, phentiramine, sulbitramine, orlistat, neuropeptide Y5 inhibitors (NP Y5 receptor antagonosts), leptin, which is a peptidic hormone, $\beta_3$ adrenergic receptor agonists, and PPARγ antagonists and partial agonists;

(h) ileal bile acid transporter inhibitors; and (i) insulin receptor activators, such as those disclosed in copending, commonly assigned U.S. application Ser. Nos. 09/095,244 and 09/280,602.

Where a second pharmaceutical is used in addition to an active compound taught herein, the two pharmaceuticals may be administered together in a single composition, separately at approximately the same time, or on separate dosing schedules. The important feature is that their dosing schedules comprise a treatment plan in which the dosing schedules overlap in time and thus are being followed concurrently.

Methods of Synthesis

The compounds of the present invention can be prepared according to the following methods.

Method A

Toluic acid derivative 1 can be treated with NBS in 1,2-dichloroethane with AIBN under light at reflux to give bromide 2. The acid can be reduced with borane in THF to provide the alcohol 3 which in turn is oxidized with $MnO_2$ to afford aldehyde 4. Di-tert-butyl phosphite can be deprotonated with a base such as $LiN(TMS)_2$ and reacted with aldehyde 4. The resulting alcohol 5 is then oxidized with $MnO_2$ to provide ketone 6. The ketone 6 is treated with DAST to afford compound 7.

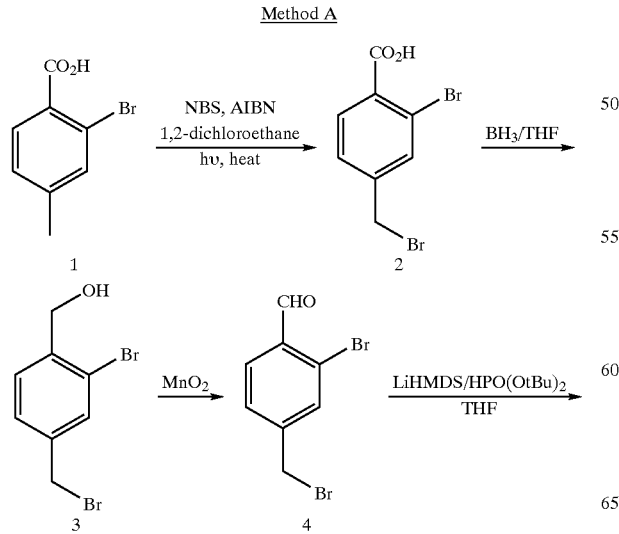

Method A-1

2-Fluoro-4-methyl aniline 8 is treated with $NaNO_2/HCl$ followed by KCN/CuCN to give nitrile 9 which in turn is hydrolyzed to give 10. Compound 10 is converted to 11 using the sequence described in Method A. Method A-1 can also be applied to the ortho chloro analog of 8.

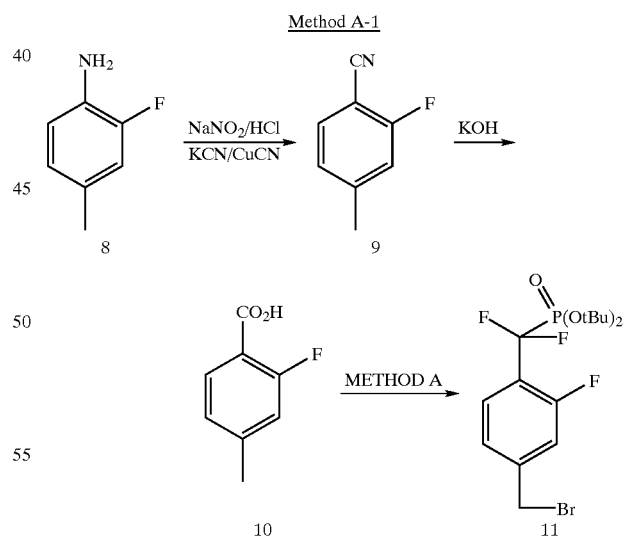

Method A-2

The methyl ester of 4-aminobenzoic acid II can be brominated with pyridinium tribromide to give III, which is treated with $NaNO_2/HCl$ and KCN/CuCN to give nitrile IV.

DIBAL reduction followed by bromination with POBr$_3$, gives VI, which is treated with lithium dialkyl phosphite to afford the phosphonate alcohol VII. Swern oxidation followed by fluorination with DAST provides the desired difluoromethyl phosphonate IX.

Compound 13 can be alkylated a second time with 7 using a base such as potassium tert-butoxide in the presence of nBu$_4$NI and 18-Crown-6 to give 14. The ester is then hydrolyzed with AcOH—H$_2$O to give acid 15.

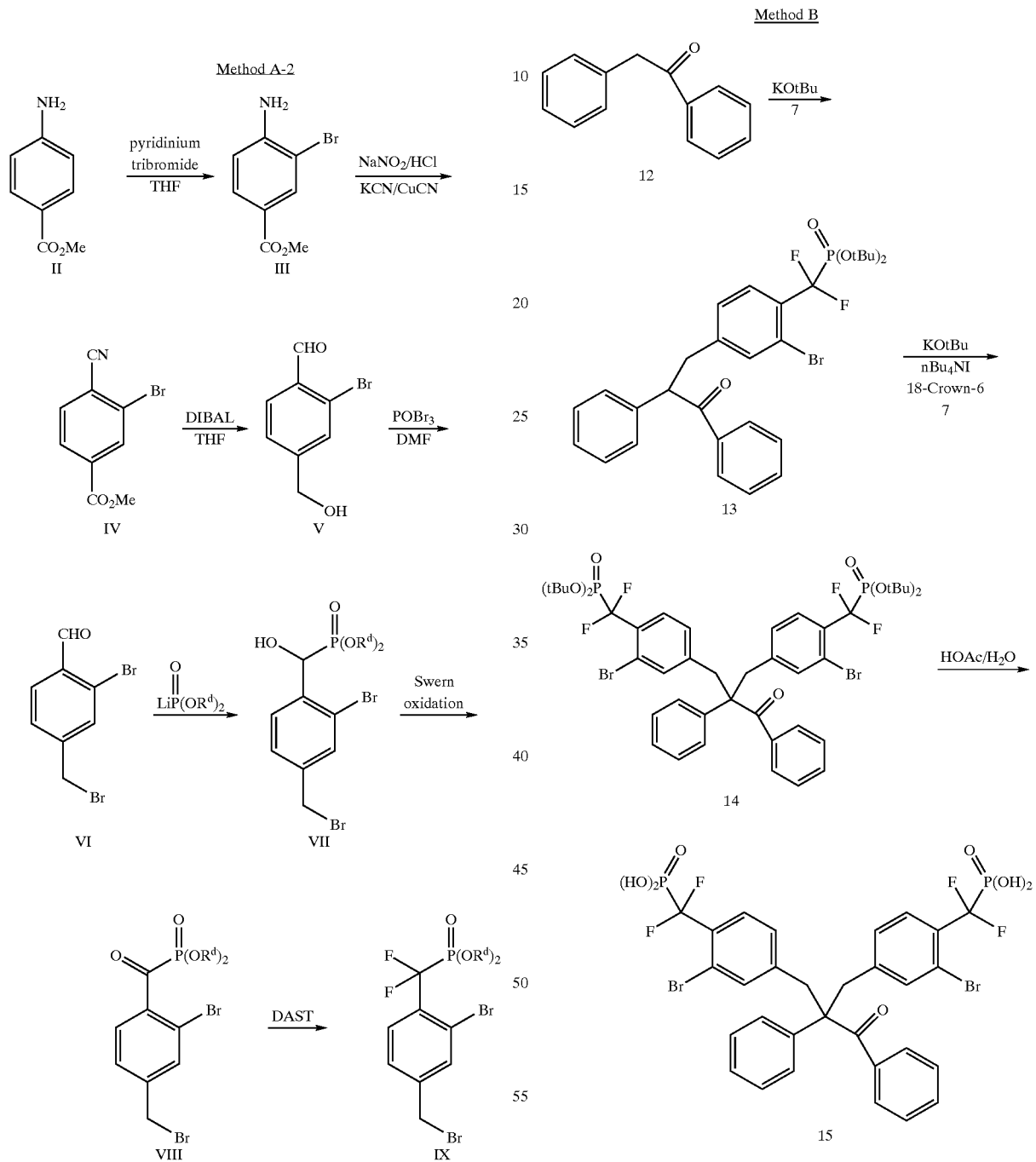

R$^d$ = Et, tBu

Method B

Deoxybenzoin 12 can be deprotonated with potassium tert-butoxide and treated with compound 7 to give 13.

Method C

Template 16 is treated with a suitable base such as NaH, KOtBu, LHMDS, or nBuLi, s-BuLi, t-BuLi, LDA or a combination of these bases followed by alkylating agent 17 to give 18. A second base treatment, followed by addition of alkylating agent 19 gives dialkylated product 20. Acid deprotection then gives the desired product I.

Method C

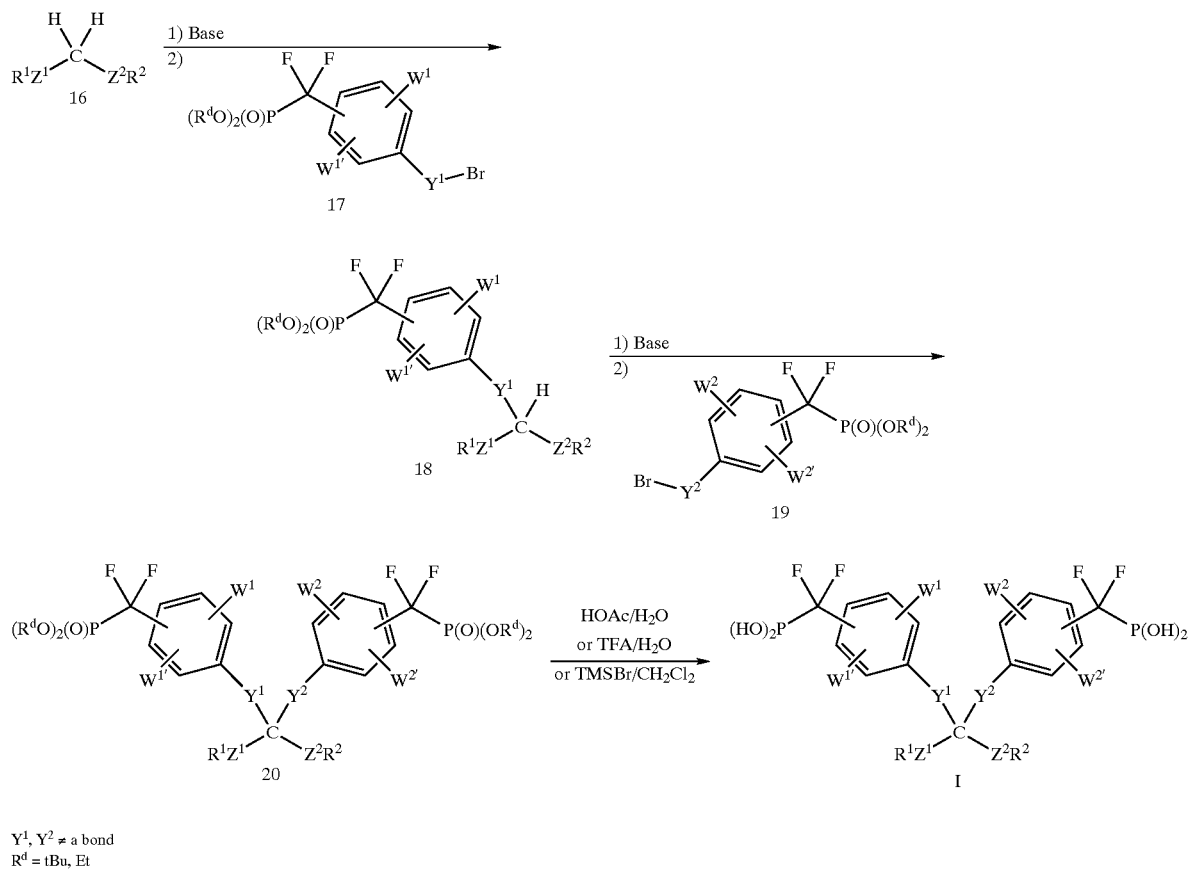

$Y^1, Y^2 \neq$ a bond
$R^d = $ tBu, Et

Method C-1

3-Bromo-4-iodotoluene 26 is converted to the benzyl bromide 27 using NBS in the presence of benzoyl peroxide at reflux in $CCl_4$ under light. Benzyl nitrile 28 is then alkylated with the benzyl bromide 27 in the presence of NaOH and phase transfer catalysis as described by D. Barbry, Synthetic Communications, 25 (19), 3007 (1995), to provide compound 29. The compound 29 can be transformed to compound 30 using diethyl (bromodifluoromethyl) phosphonate as described by T. Yokomatsu, Tetrahedron 53 (3), 815 (1997).

Method C-1

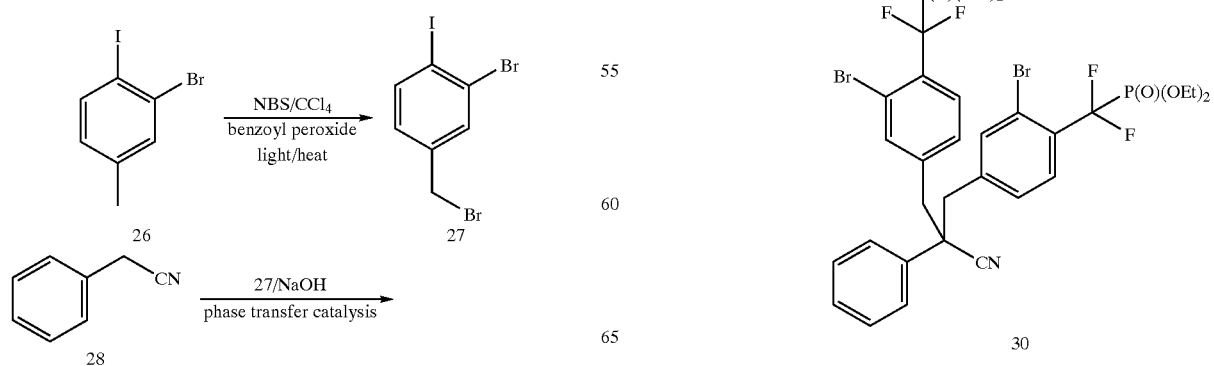

-continued

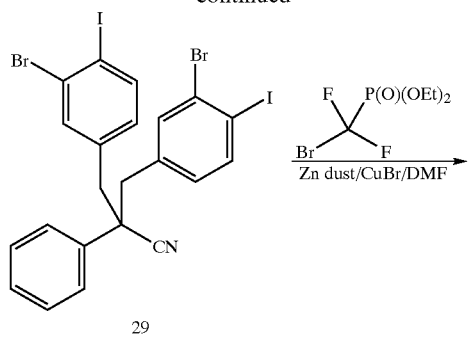

Method C-2

The nitrile 30 is treated with tris (2-perfluorohexylethyl) tin azide as described by D. P. Curran, *Tetrahedron* 55, 8997 (1999), other tin azide reagent or sodium azide, to provide compound 31. The ester is then removed with TMSBr in CHCl₃ followed by a MeOH work-up.

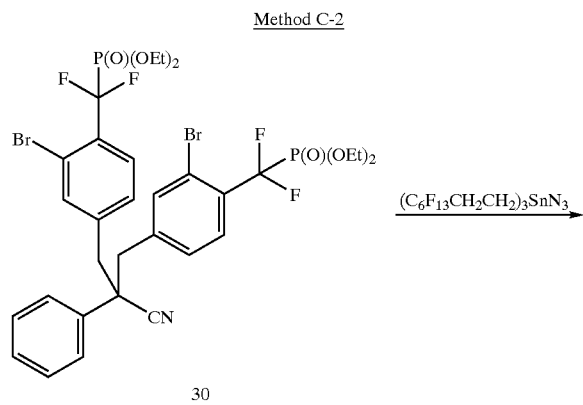

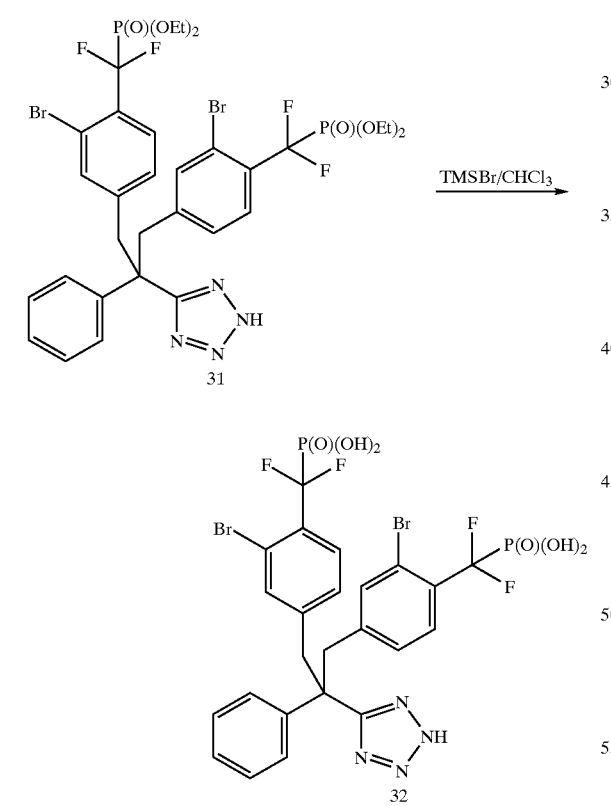

Method C-3

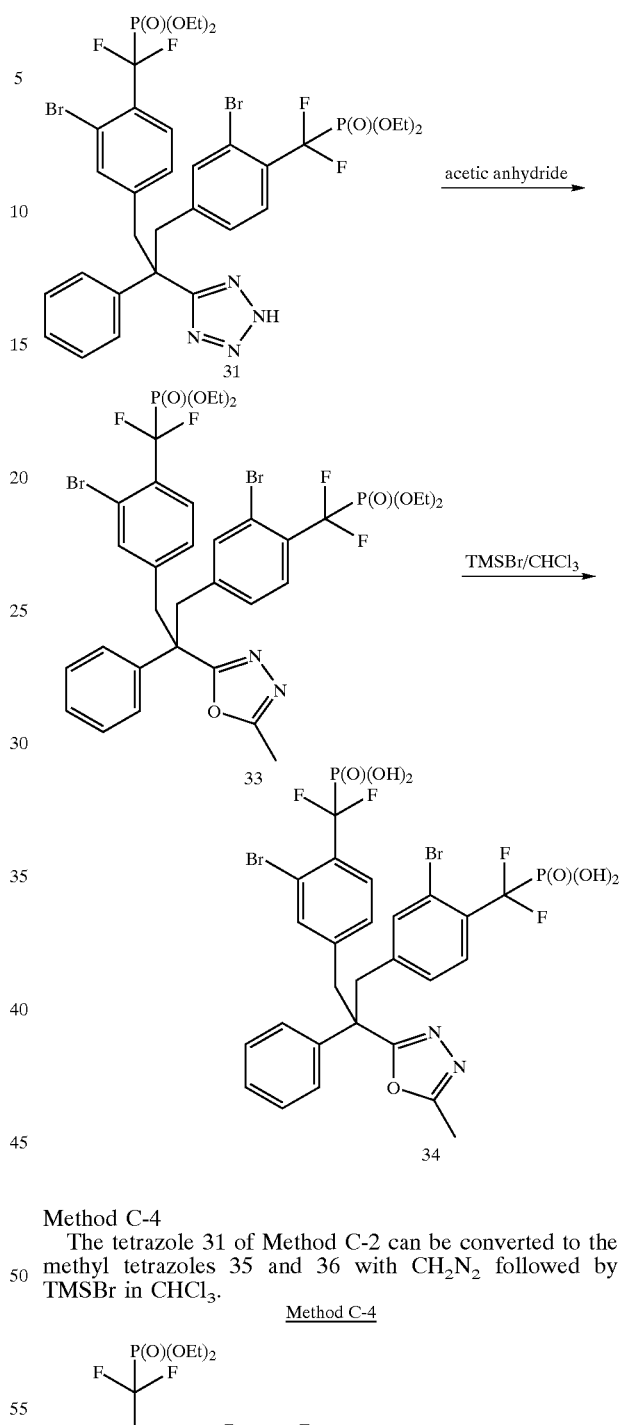

The tetrazole 31 is converted to the oxadiazole 33 as described by A. A. G Faraco, *J. Heterocyclic Chem.*, 36, 1129 (1999). The ester is then converted to the acid 34 using conditions described in Method C-2.

Method C-4

The tetrazole 31 of Method C-2 can be converted to the methyl tetrazoles 35 and 36 with CH₂N₂ followed by TMSBr in CHCl₃.

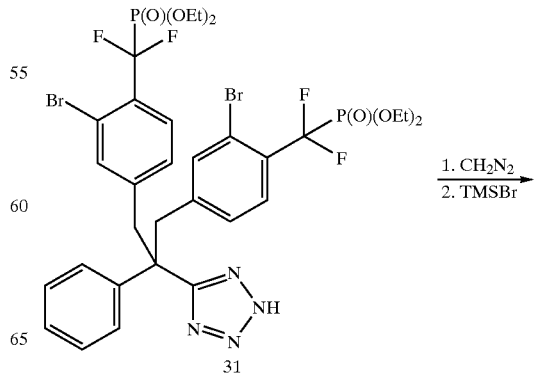

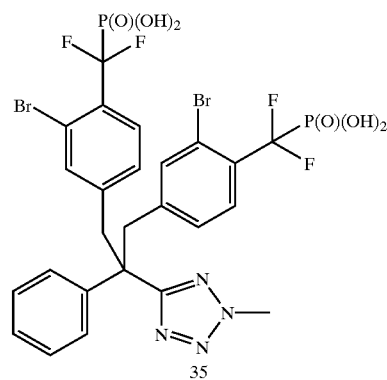
35
+
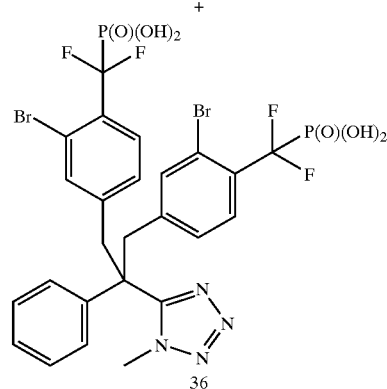
36
Method C-5
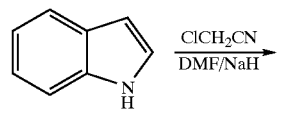
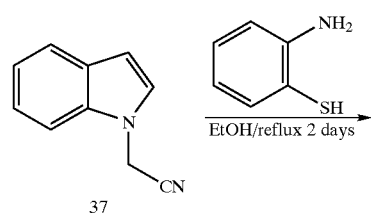
37
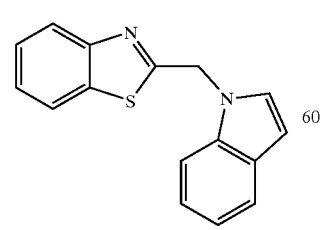
38
Method C-6
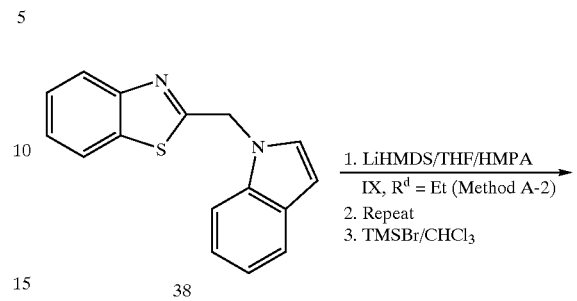
38
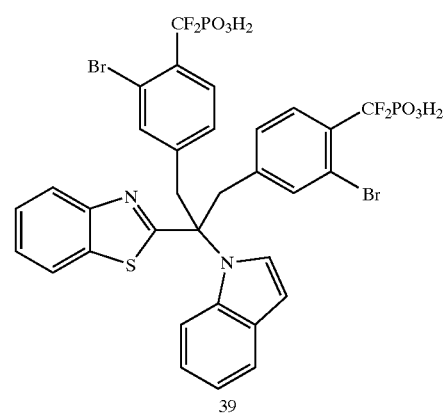
39
Method C-5
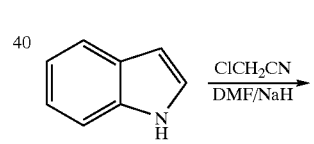
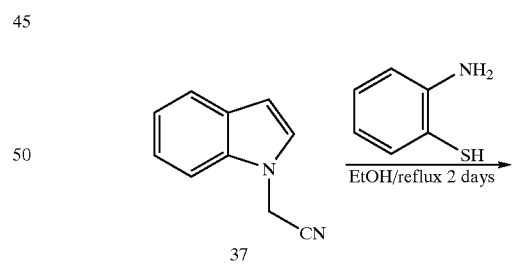
37
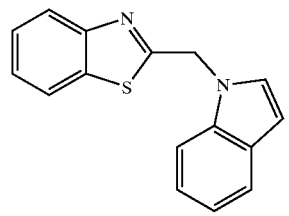
38

Method C-6

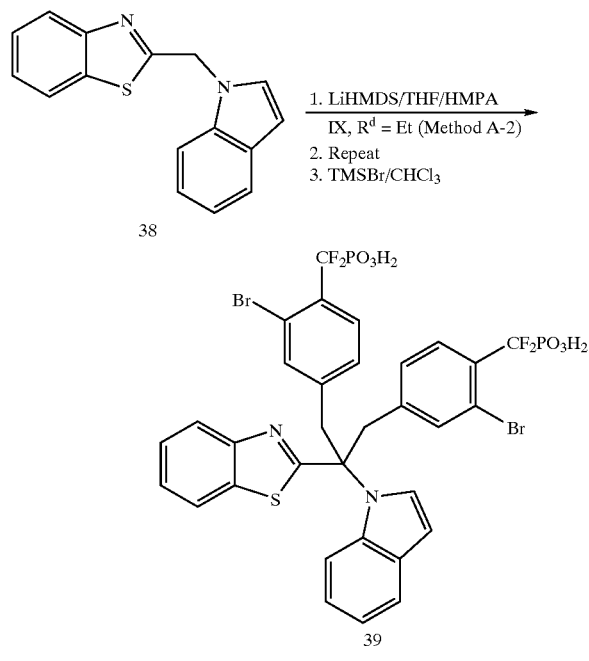

Method D

The disodium phosphonate 21 can be alkylated with a chloroalkyl ester (*Synth. Com.* 25(18) 2739 (1995)) or carbonate (*Antiviral Chemistry & Chemotherapy* 8, 557 (1997)) to give both the mono and diprotected phosphonates which can be separated by flash chromatography on silica gel. In Methods D, E and F, Q is the residue of the molecule that is attached to the —$CF_2PO_3H_2$ group.

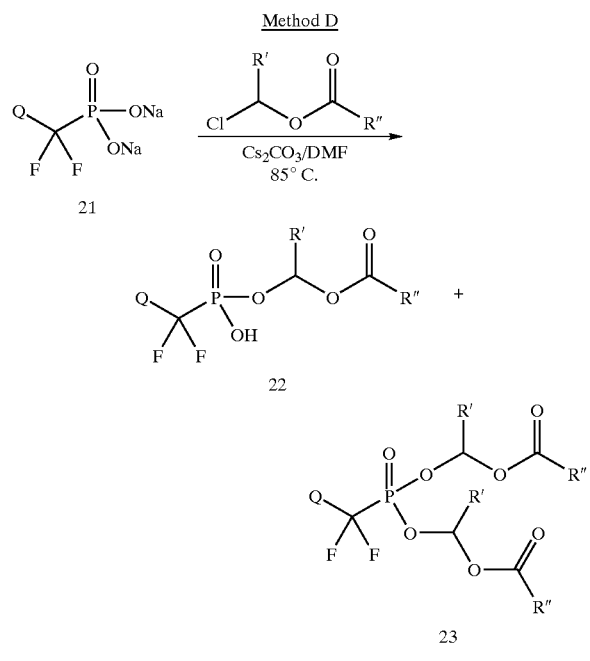

Method E

The phosphonic acid 24 can be treated with $Cs_2CO_3$ and a chloroalkyl ester or carbonate in $CH_3CN$ to give a mixture of mono and diprotected phosphonates which can be separated by flash chromatography on silica gel.

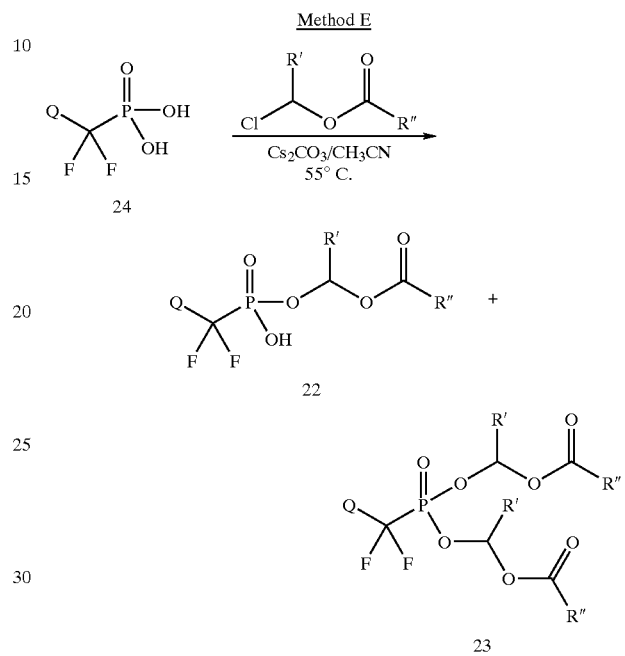

Method F

The phosphonic acid 24 can be treated with silver trifluoroacetate to give the disilver salt 25 which can be treated with an iodoalkyl ester (*Eur. J. Phar. Sci.* 4, 49 (1996)) or carbonate to give a mixture of the mono and diprotected phosphonates which are separable by flash chromatography.

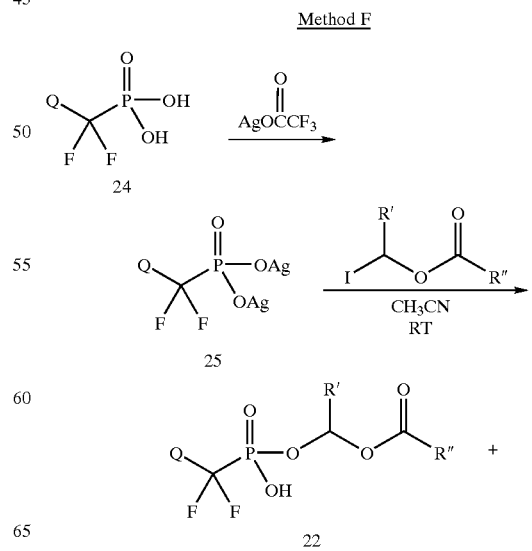

-continued
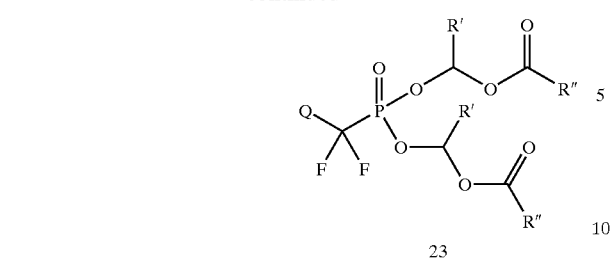
23
TABLE 1
(Table of Compounds)
| | Example | Method |
|---|---|---|
| 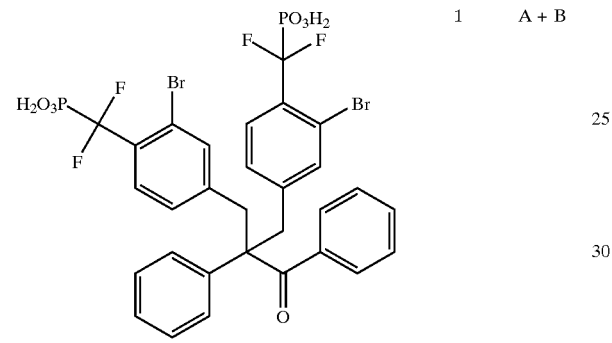 | 1 | A + B |
TABLE 2
Other Compounds of the Invention
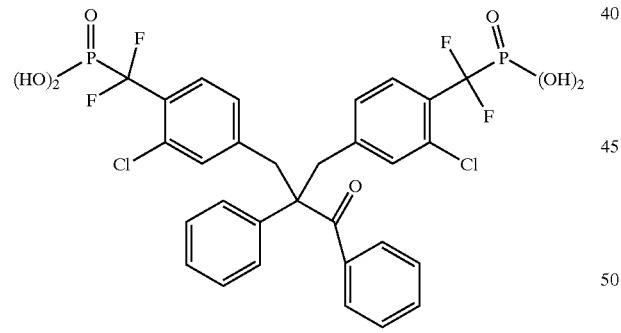
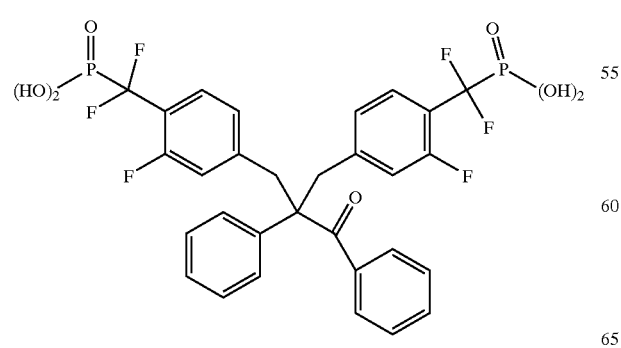
TABLE 3
Compounds Containing Heteroaromatic Substituents
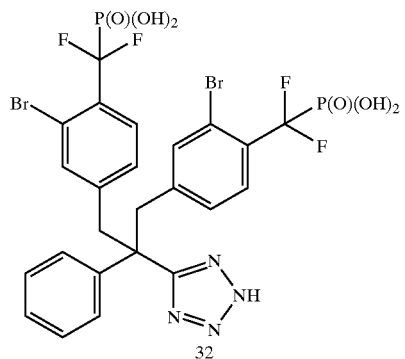
32
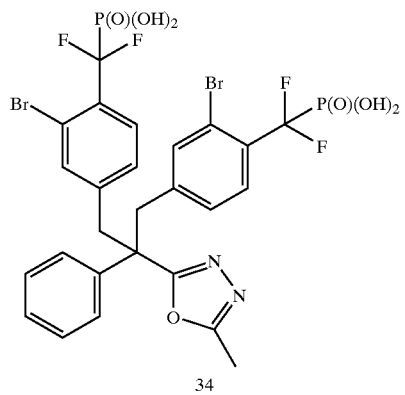
34
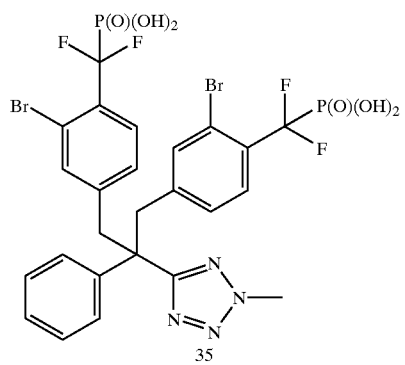
35
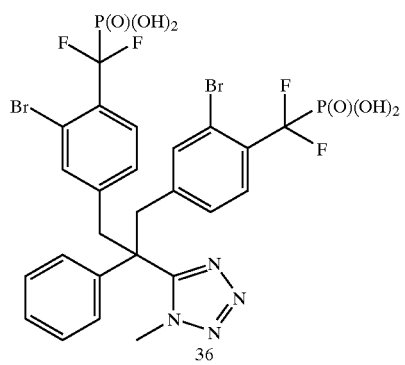
36

TABLE 3-continued
Compounds Containing Heteroaromatic Substituents
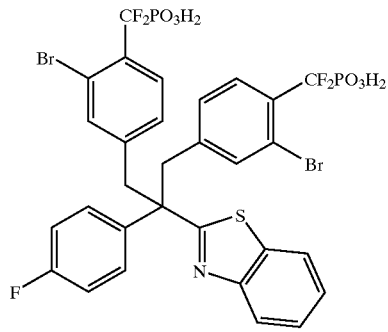
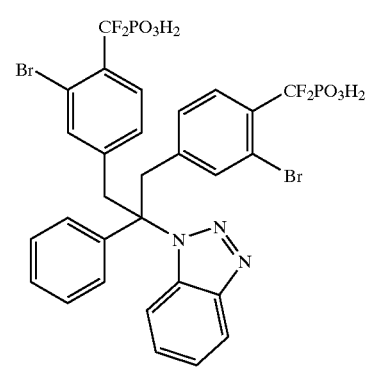
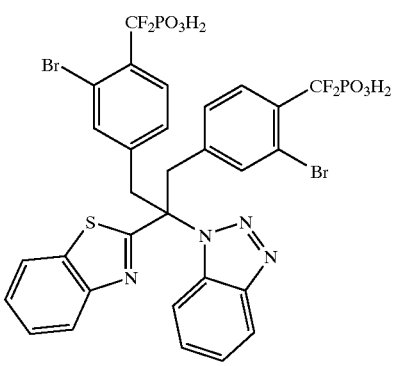
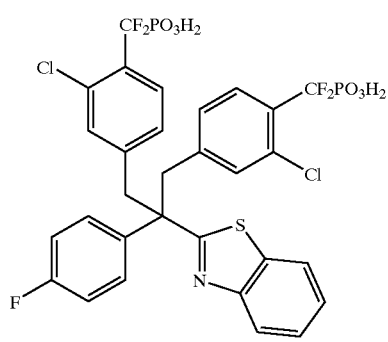
TABLE 3-continued
Compounds Containing Heteroaromatic Substituents
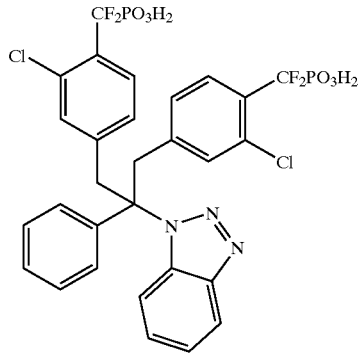
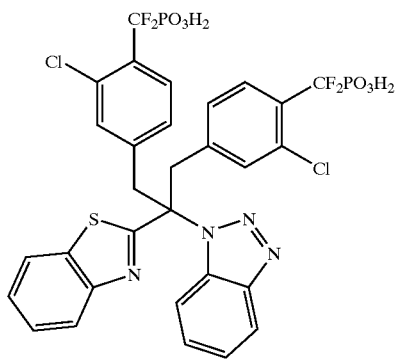
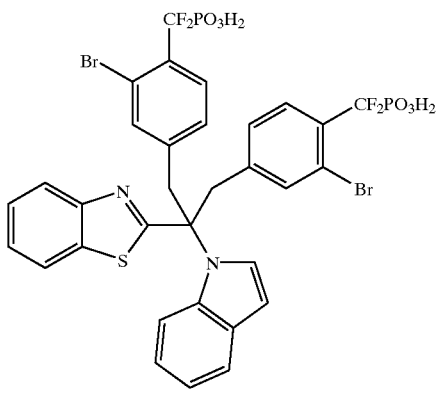
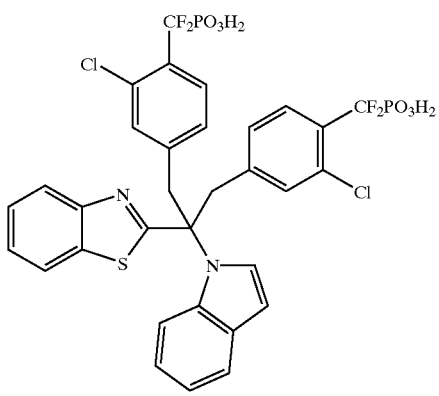

Assays for Demonstrating Biological Activity

Activity in the compounds of this application is demonstrated using the following assays for PTP-1B-inhibiting activity.

Phosphatase Assay Protocol
Materials:
EDTA—ethylenediaminetetraacetic acid (Sigma)
DMH—N,N'-dimethyl-N,N'-bis(mercaptoacetyl)-hydrazine (synthesis published in *J. Org. Chem.* 56, pp. 2332–2337, (1991) by R. Singh and G. M. Whitesides and can be substituted with DTT-dithiothreitol Bistris-2,2-bis(hydroxymethyl)2,2',2"-nitrilotriethanol-(Sigma) Triton X-100-octylphenolpoly(ethyleneglycolether) 10 (Pierce)
Antibody: Anti-glutathione S-transferase rabbit (H and L) fraction (Molecular Probes)
Enzyme: Human recombinant PTP-1B, containing amino acids 1–320, fused to GST enzyme (glutathione S-transferase) or to FLAG peptide purified by affinity chromatography (Huyer et al, 1997, J. Biol. Chem., 272, 843–852). Wild type contains active site cysteine (215), whereas mutant contains active site serine (215).
Tritiated peptide: Bz-NEJJ-CONH$_2$, Mwt. 808, empirical formula, $C_{32}H_{32}T_{12}O_{12}P_2F_4$

| Stock Solutions | |
|---|---|
| (10X) Assay Buffer | 500 mM Bistris (Sigma), pH 6.2, MW = 209.2 |
| | 20 mM EDTA (GIBCO/BRL) |
| | Store at 4° C. |
| Prepare fresh daily: | |
| Assay Buffer (1X) (room temp.) 2 mM EDTA Enzyme Dilution | 50 mM Bistris 5 mM DMH (MW = 208) |
| Buffer (keep on ice) | 50 mM Bistris |
| | 2 mM EDTA |
| | 5 mM DMH |
| | 20% Glycerol (Sigma) |
| | 0.01 mg/ml Triton X-100 (Pierce) |
| Antibody Dilution | |
| Buffer (keep on ice) | 50 mM Bistris |
| | 2 mM EDTA |

IC$_{50}$ Binding Assay Protocol:
Compounds (ligands) which potentially inhibit the binding of a radioactive ligand to the specific phosphatase are screened in a 96-well plate format as follows:
To each well is added the following solutions@25° C. in the following chronological order:
1. 110 μl of assay buffer.
2. 10 μl. of 50 nM tritiated BzN-EJJ-CONH$_2$ in assay buffer (1x)@25° C.
3. 10 μl. of testing compound in DMSO at 10 different concentrations in serial dilution (final DMSO, about 5% v/v) in duplicate@25° C.
4. 10 μl. of 3.75 μg/ml purified human recombinant GST-PTP-1B in enzyme dilution buffer.
5. The plate is shaken for 2 minutes.
6. 10 μl. of 0.3 μg/ml anti-glutathione S-transferase (anti-GST) rabbit IgG (Molecular Probes) diluted in antibody dilution buffer@25° C.
7. The plate is shaken for 2 minutes.
8. 50 μl. of protein A-PVT SPA beads (Amersham)@25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. IC$_{50}$ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 μM are defined as actives.

Enzyme Assay PTP-1B
Assay Buffer
  50 mM Bis-Tris (pH=6.3)
  2 mM EDTA
  5 mM N,N'-dimethyl-N,N'-bis(mercaptoacetyl)hydrazine (DMH)
Substrate
  10 mM fluorescein diphosphate (FDP) store at −20□C
Enzyme Dilution Buffer
  50 mM Bis-Tris (pH=6.3)
  2 mM EDTA
  5 mM DMH
  20%(v/v) glycerol
  0.01% Triton X-100

The assay was carried out at room temperature in 96 well plates. The reaction mixture in 170 μl contained 50 mM Bis-Tris (pH=6.3), 2 mM EDTA, 5 mM N,N'-dimethyl-N, N'bis(mercaptoacetyl)hydrazine (DMH) and 10 μM fluorescein diphosphare (FDP). 10 μl of 10 concentrations (serial dilution) of the test compound (inhibitor) dissolved in DMSO or DMSO alone for control was added to each well and the plate was mixed for 2 min. The reaction was initiated by adding 20 μl of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15–30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the IC$_{50}$.

Pharmacokinetics in Rats
Per Os Pharmacokinetics in Rats
Procedure:
The animals are housed, fed and cared for according to the Guidelines of the Canadian Council on Animal Care.
Male Sprague Dawley rats (325–375 g) are fasted overnight prior to each PO blood level study.
The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.
Vehicles:

The following vehicles may be used in PO rat blood level determinations:

| | |
|---|---|
| PEG 200/300/400: | restricted to 2 mL/kg |
| Methocel 0.5%–1.0%: | 10 mL/kg |
| Tween 80: | 10 mL/kg |

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \ (mg/kg)}{AUCiv}$$

The units of CL are mL/k·kg (milliliters per hour kilogram)
Intravenous Pharmacokinetics in Rats
Procedure:

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.
Vehicles:

The following vehicles may be used in IV rat blood level determinations:

| | |
|---|---|
| Dextrose: | 1 mL/kg |
| 2-Hydroxypropyl-b-cyclodextrin | 1 mL/kg |
| DMSO (dimethylsulfoxide): | Restricted to a dose volume of 0.1 mL per animal |
| PEG 200: | Not more than 60% mixed with 40% sterile water-1 mL/kg |

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv \ (mg/kg)}{AUCiv}$$

The units of CL are mL/h·kg (milliliters per hour kilogram).

PTP 1B Intact Cell Assay

This assay is the subject of copending, commonly assigned U.S. Provisional Application No. 60/123,243, filed Mar. 8, 1999, which patent application is incorporated herein by reference, and was recently published in Cromlish, Wanda A., Paul Payette and Brian P. Kennedy (1999) *Biochem Pharmocol* 58: 1539–1546.
Construction of Recombinant Baculovirus Transfer Vectors and Insect Cells Briefly, using the Bac-to-Bac Baculovirus Expression System (Gibco-BRL, Mississauga, Ontario, Canada) PTP 1B cDNA (obtained from Dr. R. L. Erikson, Harvard University, USA), is cloned into the pFASTBAC donor plasmid engineered to include a FLAG sequence at the 5' end of the cDNA (PTP1B-FL). The recombinant plasmid is transformed into competent DH10BAC *E. Coli* cells. Following transposition and antibiotic selection, the recombinant bacmid DNA is isolated from selected *E. Coli* colonies and used to transfect sf9 insect cells (Invitrogen, San Diego, Calif., U.S.A.). The sf9 cells are cultured in spinner flasks at 28° C. in Graces supplemented medium (Gibco-BRL, Mississauga, Ontario, Canada) with 10% heat-inactivated fetal bovine serum (Gibco-BRL) following the protocol of Summers and Smith (*A manual for Methods for Baculovirus Vectors and Insect Culture Procedures*(*Bulletin No.* 1555). Texas A & M University, Texas Agricultural Experiment Station, College Station, Tex., 1987).

Intact Cell Assay

Infected sf9 cells expressing PTP1B-FL and mock infected cells, are harvested at 29 hpi (hours post infection) by gentle centrifugation (Beckman GS-6R) at 460 rpm, (48 g) for 5 min. Cells are washed once in assay buffer (Hanks' solution buffered with 15 mM Hepes, pH 7.4, obtained from Sigma, St. Louis, Mo., U.S.A.) and recentrifuged at 300 rpm (21 g) for 10 min. The cells are then gently resuspended in assay buffer and examined using a hemacytometer for cell density and viability by trypan blue exclusion. Assays are performed using a Tomtec Quadra 96 pipeting robot, programmed to mix the cells gently after each addition. In 200 $\mu$L of assay buffer, $2 \times 10^5$ PTP expressing cells or mock infected cells are dispensed into each well of 96-well polypropylene plates and pre-incubated either with a test compound or DMSO vehicle (3 $\mu$L), for 15 min at 37° C. The pre-incubated cells are challenged with a final concentration of 10 mM pNPP (p-nitrophenyl phosphate, obtained from Sigma-Aldrich Canada Ltd., Oakville, Ontario) for 15 min, centrifuged at 4° C. and the amount of substrate hydrolysis is determined spectrophotometerically at $OD_{405}$.

Oral Glucose Tolerance Test

Oral glucose tolerance tests are done on conscious Zucker obese fa/fa rats or obese ob/ob mice (age 12 weeks or older). The animals are fasted for 16–18 hours before use for experiments. A test compound or a vehicle is given either intraperitoneally or orally 60 minutes before oral administration of a glucose solution at a dose of 2 g/kg body weight. Blood glucose levels are measured using a Medisense glucometer from tail bled samples taken at different time points before and after administration of glucose. A time curve of the blood glucose levels is generated and the area-under-the-curve (AUC) for 120 minutes is calculated (the time of glucose administration being time zero). Percent inhibition is determined using the AUC in the vehicle-control group as zero percent inhibition.

In separate studies, C57BL/6J mice are fed a high fat (35%) and high carbohydrate (36%) diet obtained from Bioserv (Frenchtown, N.J.) for 3 to 4 weeks, at which time the mice gained 50–100% of the baseline body weight. Oral glucose tolerance tests are done in the same manner as described above.

EXAMPLES

The invention is further illustrated by the following examples, which are provided to illustrate the invention and are not to be construed as limiting the invention in any way. The following experimental methods were generally followed, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram (s)), mg (milligrams(s)), mol (moles), mmol (millimoles), eq (equivalent(s)).

Example 1

[2-bromo-4-(2-{3-bromo-4-[difluoro(phosphono)methyl] benzyl}-3-oxo-2,3-diphenylpropyl)phenyl](difluoro) methylphosphonic acid Step 1 2-bromo-4-(bromomethyl)benzoic acid 2-Bromo-4-methylbenzoic acid (33.5 g, 156 mmol, 1 eq) and N-Bromosuccinimide (40.7 g, 233 mmol, 1.5 eq) were dissolved in refluxing 1,2-dichloroethane (600 ml) and a catalytic amount of AIBN was added. The mixture was left stirring under a lamp and under nitrogen for 1 hour. The solvent was removed and the mixture was partitioned between 600 ml of water and 600 ml EtOAc. The organic layer was washed twice with water (600 ml), washed once with brine (600 ml) and then dried with sodium sulfate. The solvent was removed and the crude mixture was triturated with 10% EtOAc/Hexane for 2 hours and 23.8 g (52%) of the title compound was obtained.

Step 2 [2-bromo-4-(bromomethyl)phenyl)methanol

The compound of Step 1 (23.8 g, 81 mmol, 1 eq) was dissolved in THF under nitrogen at 0° C. A 1M borane solution in THF (242 ml, 242 mmol, 3 eq) was then added dropwise and the mixture was stirred at r.t. for 1 h. under nitrogen. The solution was cooled in an ice bath and 125 ml of methanol was then added slowly. The solvents were removed and the mixture partitioned between 400 ml of water and 400 ml of 20% THF/EtOAc. The aqueous layer was washed 3 times with 400 ml of 20% THF/EtOAc and the combined organic layer was dried with sodium sulfate. The solvent was removed and 19.7 g (87%) of the title compound was obtained.

Step 3 4-(bromomethyl)-2-bromobenzaldehyde

The compound of Step 2 (8 g, 29 mmol, 1 eq) was dissolved in 10% EtOH/EtOAc (300 ml) and 5 eq of $MnO_2$ (12.4 g, 142 mmol) was added every hour for 6 hours. The mixture was filtered through Celite and the solvent was removed under vacuum to give 6.5 g (80%) of the title compound.

Step 4 di(tert-butyl) [2-bromo-4-(bromomethyl)phenyl] (hydroxy)methylphosphonate Di-tert-butyl phosphite (14.8 g, 76.3 mmol, 1.05 eq) was dissolved in 200 ml THF at −78° C. under nitrogen and 72 ml (1.05 eq) of 1.06M Lithium bis(trimethylsilyl)amide in THF was added over 30 min. The mixture was left stirring at −78° C. under nitrogen for 30 min and then added to a solution of the compound of Step 3 (20.2 g, 72.7 mmol, 1 eq) in 200 ml THF at −78° C. The solution was warmed to 0° C. and then poured into 400 ml of half saturated aqueous ammonium acetate. The layers were separated and the aqueous layer was washed with 400 ml isopropyl acetate. The organic layers were combined, dried with sodium sulfate and the solvent removed. The crude solid was then triturated with 15% EtOAc/hexane for 2 hours and 30.4 g (89%) of the title compound was obtained.

Step 5 di-(tert-butyl)-2-bromo-4-(bromomethyl) benzoylphosphonate

The compound of Step 4 was dissolved in acetone, and $MnO_2$ (40 equiv.) was added. The mixture was stirred vigorously for 2–7 hours, then filtered through Celite. The solvent was removed to provide the title compound. Alternatively, the title compound can be prepared by Swern oxidation of the compound of Step 4.

Step 6 di(tert-butyl)[2-bromo-4-(bromomethyl)phenyl](difluoro)methylphosphonate

To di(tert-butyl)-2-bromo-4-(bromomethyl) benzoylphosphonate (8.0 g, 17 mmol) was added 2-methyl-2-butene (8.0 mL). To this mixture at 0° C. was added diethylamino sulfur trifluoride (40 mL). After a period of 24 h, the reaction mixture was poured over 2.2L of 1/1 ethylacetate-hexane, diisopropylethylamine (90 mL) and saturated $NaHCO_3$ (400 mL) at 0° C. The organic phase was separated, dried over $Na_2SO_4$, filtered and evaporated. The crude material was purified by flash chromatography (20% ethyl acetate in hexane) over silica gel previously washed with 20% ethyl acetate hexane containing 1% of $Et_3N$ to give 5.0 g of the title compound.

$^1$H NMR (400 MHz, $CDCl_3$) δ 1.50 (18H, s), 4.40 (2H, s), 7.40 (1H, d), 7.60 (1H, d), 7.65 (1H, d).

Step 7 di(tert-butyl)[2-bromo-4-(3-oxo-2,3-diphenylpropyl)phenyl](difluoro)methylphosphonate To a solution of 2-deoxybenzoin (174 mg, 0.88 mmol) and di(tert-butyl)[2-bromo-4-(bromomethyl)phenyl](difluoro)methylphosphonate (290 mg, 0.59 mmol) in DMF (5 mL) at 0° C. was added NaH (28 mg, 0.94 mmol), 80% in oil). After 20 min at 0° C., the ice bath was removed and the mixture was stirred at r.t. for 1 h. Saturated $NH_4Cl$ solution was then added and the product was extracted with $Et_2O$. The organic layer was washed with $H_2O$ and brine, and was then dried ($MgSO_4$), filtered, and evaporated. The residue was stirred vigourously in 1:5 $Et_2O$:hexane for 1.5 h. After filtration, the stirring was repeated a second time to give a white solid (255 mg).

$^1$H NMR ($CD_3COCD_3$) δ 1.41 (18H, s), 3.10–3.17 (1H, m), 3.50–3.57 (1H, m), 5.19–5.25 (1H, m), 7.15–7.21 (1H, m), 7.23–7.32 (3H, m), 7.32–7.46 (5H, m), 7.47–7.54 (1H, m), 7.56–7.59 (1H, m), 7.99–8.05 (2H, m).

Step 8: di(tert-butyl)[2-bromo-4-(2-{3-bromo-4-[[di(tert-butoxy) phosphoryl](difluoro)methyl]benzyl}-3-oxo-2,3-diphenylpropyl)phenyl](difluoro)methylphosphonate To a solution of the product from Step 7 (255 mg, 0.4 mmol), 18-Crown-6 (55 mg, 0.2 mmol), and $Bu_4NI$ (16 mg, 0.04 mmol) in THF (4 mL) at −78° C. was added KOtBu (0.5 mL, 0.5 mmol, 1.0 M in THF). After 15 min at −78° C., a solution of di(tert-butyl)[2-bromo-4-(bromomethyl)phenyl) (difluoro)methylphosphonate (207 mg, 0.4 mmol) in THF (1 mL) was added via double-tipped needle. The cold bath was then removed and the reaction mixture was stirred at r.t. for 1.5 h. After quenching with saturated $NH_4Cl$ solution, a standard aqueous work-up was carried out. The product was purified by flash chromatography (1:3 EtOAc:hexane containing 1% $Et_3N$) to give an off-white solid (96 mg).

$^1$H NMR ($CD_3COCD_3$) δ 1.50 (36H, s), 3.47–3.67 (4H, m), 6.98–7.05 (4H, m), 7.16–7.23 (2H, m), 7.30–7.45 (7H, m), 7.46–7.54 (1H, m), 7.61–7.66 (2H, m).

Step 9: [2-bromo-4-(2-{3-bromo-4-[difluoro(phosphono)methyl]benzyl}-3-oxo-2,3-diphenylpropyl)phenyl](difluoro) methylphosphonic acid The product of Step 8 (96 mg, 0.094 mmol) was stirred overnight in HOAc (3 mL) and $H_2O$ (0.3 mL). The solvent was removed under vacuum and the residue was co-evaporated with toluene/acetone (3×) to give a tan coloured foam (85 mg).

$^1$H NMR ($CD_3COCD_3$) δ 3.46–3.62 (4H, m), 5.10–5.60 (4H, br), 6.94–7.03 (4H, m), 7.18–7.27 (2H, m), 7.29–7.52 (8H, m), 7.59–7.65 (2H, m).

What is claimed is:

1. A compound represented by formula I:

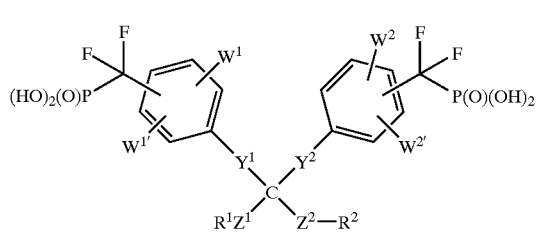

or a pharmaceutically acceptable salt thereof, wherein:

$R^1$ and $R^2$ are selected from the group consisting of: $C_{1-10}$alkyl$(R^a)_{0-7}$, $C_{2-10}$alkenyl$(R^a)_{0-7}$, Aryl$(R^a)_{0-3}$ and Het$(R^a)_{0-3}$;

wherein each $R^a$ independently represents a member selected from the group consisting of: Aryl, OH, halogen, CN, $CO_2H$, $CO_2C_{1-6}$alkyl, $CO_2C_{2-6}$alkenyl, $OC_{1-10}$alkyl, $C(O)C_{1-6}$alkyl, $S(O)_yC_{1-6}$alkyl, $C_{1-6}$alkyl, $C_{1-6}$haloalkyl, $S(O)_yNR^{3'}R^{4'}$, wherein y is 0, 1, or 2, $C(O)NR^{3'}R^{4'}$, and $NR^{3'}R^{4'}$, wherein each alkyl group in $R^a$ is optionally substituted with 1–7 groups independently selected from halogen, $OC_{1-3}$ alkyl, $CO_2H$, and $CO_2C_{1-3}$alkyl, and each Aryl in $R^a$ is optionally substituted with 1–3 groups independently selected from $C_{1-3}$alkyl, halogen, $OC_{1-3}$ alkyl, $CO_2H$, and $CO_2C_{1-3}$alkyl;

Aryl is a 6–14 membered carbocyclic aromatic ring system comprising 1–3 phenyl rings, wherein the phenyl rings are fused together when there is more than one aromatic ring;

Het represents a 5-membered heterocyclic aromatic ring which is optionally benzo fused, wherein the 5-membered heterocyclic aromatic ring comprises 1–4 heteroatoms, 0–4 of which are N atoms and 0–2 of which are O or S(O)y wherein y is 0–2, and 0–2 carbonyl groups;

$Y^1$, $Y^2$, $Z^1$, and $Z^2$ each independently represents —$(CR^3R^4)_a$—X—$(CR^3R^4)_b$— wherein a and b are integers 0–2 such that the sum of a and b equals 0, 1, 2, or 3;

X represents a bond, O, $S(O)_y$, $NR^{3'}$, C(O), OC(O), C(O)O, $C(O)NR^{3'}$, $NR^{3'}C(O)$ or —CH=CH—, where y is as previously defined;

$R^3$ and $R^4$ are independently H, halogen, $C_{1-10}$alkyl or $C_{1-10}$haloalkyl;

$R^{3'}$ and $R^{4'}$ are each independently selected from the group consisting of: H, $C_{1-6}$alkyl, $C_{1-6}$haloalkyl, OH, $C(O)C_{1-6}$ alkyl, C(O)Aryl, $C(O)C_{1-6}$ haloalkyl, and Aryl;

$W^1$ and $W^2$ are each in a position on the aromatic ring adjacent to the —$CF_2P(O)(OH)_2$ substituent and are each independently selected from the group consisting of: OH, CN, halo, $OC_{1-6}alkyl(R^a)_{0-7}$, $S(O)_yC_{1-6}alkyl(R^a)_{0-7}$, with y equal to 0–2, $S(O)_3H$, $C_{1-6}alkyl(R^a)_{0-7}$, $CO_2H$, $CO_2C_{1-6}alkyl(R^a)_{0-7}$, $CO_2C_{2-6}$ alkenyl$(R^a)_{0-7}$, $C(O)C_{1-6}alkyl(R^a)_{0-7}$, $C(O)NR^{3'}R^{4'}$, $S(O)_yNR^{3'}R^{4'}$, $NR^{3'}R^{4'}$, and Aryl, wherein $R^{3'}$ and $R^{4'}$ are as defined above; and $W^{1'}$ and $W^{2'}$ are optionally present on any remaining position on the aromatic ring and are each independently selected from H and from the same groups as $W^1$ and $W^2$, wherein at least one group on $R^1$ or $R^2$ in FIG. I is selected from $Het(R^a)_{0-3}$.

2. A compound in accordance with claim 1 wherein $W^{1'}$ and $W^{2'}$ are each independently selected from the group consisting of:
   (a) hydrogen,
   (b) halogen,
   (c) $OC_{1-6}alkyl(R^a)_{0-7}$,
   (d) $SC_{1-6}alkyl(R^a)_{0-7}$,
   (e) $C_{1-6}alkyl(R^a)_{0-7}$,
   (f) $CO_2H$,
   (g) $CO_2$—$C_{1-6}alkyl(R^a)_{0-7}$,
   (h) OH,
   (i) $N(R^{3'})(R^{4'})$ and
   (j) $C(O)C_{1-6}alkyl(R^a)_{0-7}$, and
   each $W^1$ and $W^2$ are independently selected from the group consisting of:
   (a) halogen,
   (b) $OC_{1-6}alkyl(R^a)_{0-7}$,
   (c) $SC_{1-6}alkyl(R^a)_{0-7}$,
   (d) $C_{1-6}alkyl(R^a)_{0-7}$,
   (e) $CO_2H$,
   (f) $CO_2$—$C_{1-6}alkyl(R^a)_{0-7}$,
   (g) OH,
   (h) $N(R^{3'})(R^{4'})$ and
   (i) $C(O)C_{1-6}alkyl(R^a)_{0-7}$.

3. A compound in accordance with claim 1, wherein each $W^{1'}$ and $W^{2'}$ represents H, and $W^1$ and $W^2$ each independently represents a halogen, $C_{1-3}$ alkyl, $C_{1-3}$ fluoroalkyl, $OC_{1-3}$alkyl or $OC_{1-3}$ fluoroalkyl.

4. A compound in accordance with claim 3 wherein $W^1$ and $W^2$ each represents Br.

5. A compound in accordance with claim 1 wherein Het is selected from the group consisting of: tetrazole, oxadiazole, benzotriazole, benzothiazole, and indole.

6. A compound in accordance with claim 1 wherein:
   $Y^1$, $Y^2$, $Z^1$ and and $Z^2$ are each independently selected from the group consisting of:
   (a) —$CH_2$—,
   (b) —O—$CH_2$—,
   (c) —$CH_2$—O—,
   (d) —$CH_2$—O—$CH_2$—,
   (e) —S—$CH_2$—,
   (f) —$CH_2$—S—,
   (g) —$CH_2$—S—$CH_2$—,
   (h) —$S(O)_2$—$CH_2$—,
   (i) —$CH_2$—$S(O)_2$—,
   (j) —$CH_2$—$S(O)_2$—$CH_2$—,
   (k) —$S(O)_2$—,
   (l) —S—,
   (m) —O—,
   (n) —$NR^{3'}$—,
   (o) C(O), and
   (p) a direct bond.

7. A compound in accordance with claim 1 wherein $Y^1$, $Y^2$, $Z^1$ and $Z^2$ are each independently selected from the group consisting of: (a) —$CH_2$—, (b) —O—$CH_2$—, (c) —$CH_2$—O—, (d) —$CH_2$—O—$CH_2$—, (e) —S—$CH_2$—, (f) —$CH_2$—S— and (g) —$CH_2$—S—$CH_2$—.

8. A compound in accordance with claim 1 wherein $Y^1$, $Y^2$, $Z^1$, and $Z^2$ are each independently selected from the group consisting of C(O), $CH_2$, and a direct bond.

9. A compound in accordance with claim 8 wherein $Z^1$ is a direct bond, $Z^2$ is C(O), and $Y^1$ and $Y^2$ are each $CH_2$.

10. A compound in accordance with claim 1 wherein $R^1$ and $R^2$ are each independently selected from the group consisting of:
   (a) $C_1$–$C_{10}$ alkyl,
   (b) $C_1$–$C_{10}$ fluoroalkyl,
   (c) unsubstituted, mono-, di- or tri-substituted phenyl wherein the optional substituents are selected from the group consisting of:
      (1) halo,
      (2) $C_{1-10}$alkoxy,
      (3) $C_{1-6}$alkylthio,
      (4) $CF_3$,
      (5) $C_{1-6}$alkyl,
      (6) —$CO_2H$
      (7) —$CO_2$—$C_{1-4}$alkyl, and
      (8) unsubstituted, mono-, di-, or trisubstituted phenyl, wherein the optional substituents are selected from the groups in (c)(1)–(7) of this claim; and
   (d) unsubstituted, mono-, di- or tri-substituted Het, wherein the optional substituents are selected from the group consisting of:
      (1) halo,
      (2) $C_{1-10}$alkoxy,
      (3) $C_{1-6}$alkylthio,
      (4) $CF_3$,
      (5) $C_{1-6}$alkyl,
      (6) —$CO_2H$,
      (7) —$CO_2$—$C_{1-4}$alkyl, and
      (8) unsubstituted, mono-, di-, or tri-substituted phenyl, wherein the optional substituents are selected from the groups in (d)(1)–(7) of this claim; and
   wherein at least one $R^1$ and $R^2$ is selected from (d).

11. A compound in accordance with claim 10 wherein: $R^1$ and $R^2$ are each independently selected from the group consisting of phenyl and Het, wherein each phenyl and Het is optionally substituted with 1–3 substituents independently selected from $C_{1-3}$ alkyl, $C_{1-3}$ fluoroalkyl and halogen, wherein at least one of R1 and R2 is selected from Het.

12. A compound in accordance with claim 1, wherein $R^1$ is Het and $R^2$ is phenyl, wherein phenyl and Het are optionally substituted with 1–3 $R^a$ groups.

13. A compound in accordance with claim 8 wherein $R^1$ and $R^2$ are each Het, wherein Het is optionally substituted with 1–3 $R^a$ groups.

14. A compound in accordance with claim 13, wherein $W^{1'}$ and $W^{2'}$ are each H, and $W^1$ and $W^2$ are each Br.

15. A compound in accordance with claim 1 having the following structure, or a pharmaceutically acceptable salt thereof:

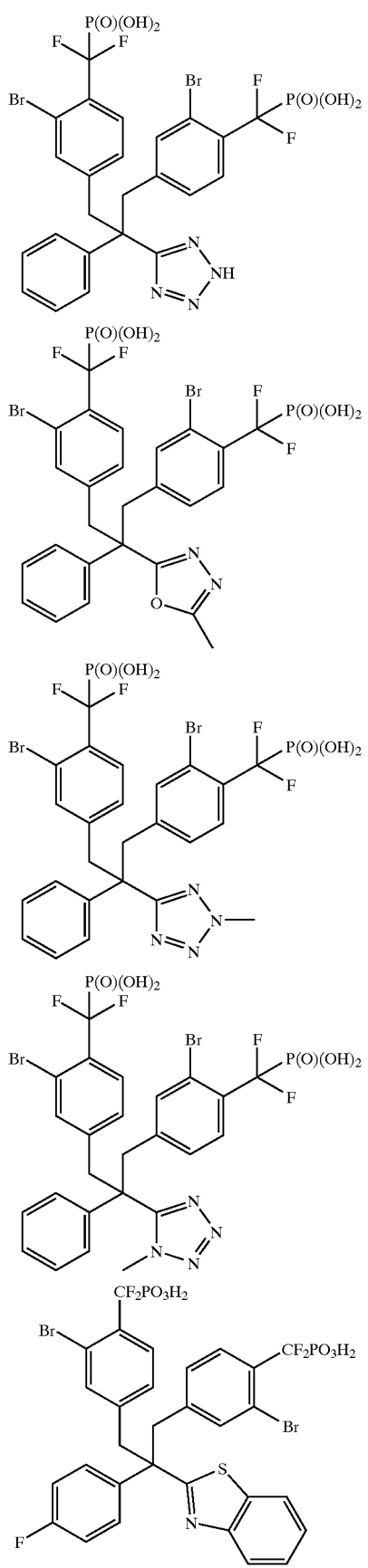
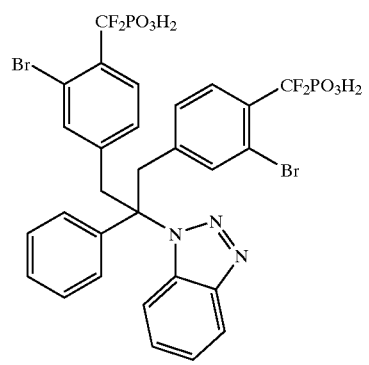
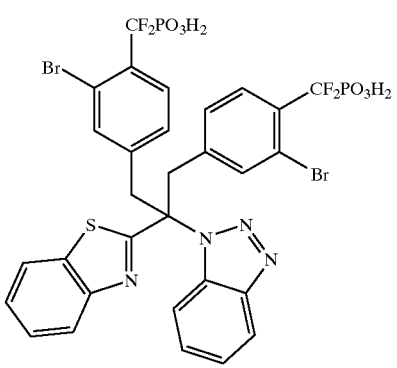
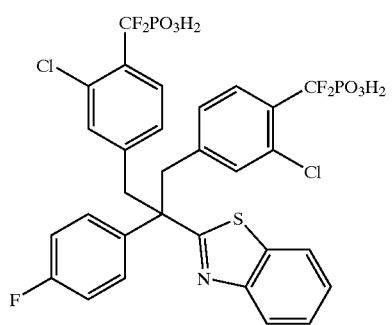
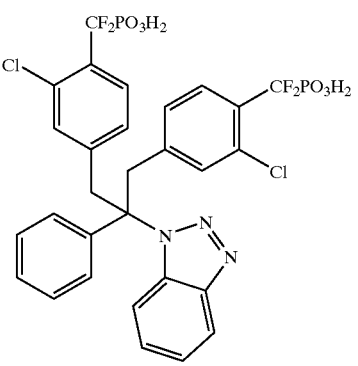

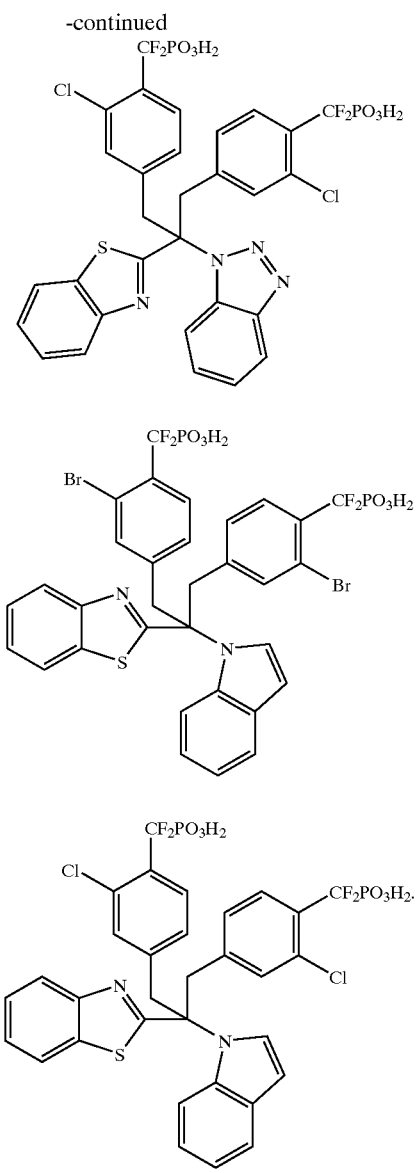

16. A compound having the formula Ia, or a pharmaceutically acceptable salt thereof:

$$\text{Ia}$$

Wherein all substituent groups other than G are as defined in claim 1, wherein one group G is selected from phenyl, —CHR'phenyl and —CHR'OC(=O)R", and the remaining three groups G are independently selected from H, phenyl, —CHR'phenyl and —CHR'OC(=O)R", wherein each R' is H or $C_{1-6}$alkyl, and each R" is —$C_{1-6}$alkyl or —O$C_{1-6}$alkyl, wherein $C_{1-6}$alkyl and —O$C_{1-6}$alkyl in each occurrence is optionally substituted with one or more substituents independently selected from 1–5 halogen atoms, a phenyl group, or a mixture of these, and each phenyl in each occurrence is optionally substituted with 1–3 substituents independently selected from halogen, —$CH_3$, —$CF_3$, —$OCH_3$ and —$OCF_3$.

17. A compound as recited in claim 16, wherein all substituent groups G that are not H are the same.

18. A pharmaceutical composition which is comprised of a compound in accordance with claim 1 in combination with a pharmaceutically acceptable carrier.

19. A method of treating or controlling diabetes and complications thereof in a mammalian patient in need of such treatment comprising administering to said patient an anti-diabetic effective amount of a compound in accordance with claim 1.

20. A method of treating or controlling obesity in a mammalian patient in need of such treatment comprising administering to said patient an anti-obesity effective amount of a compound in accordance with claim 1.

21. A method of treating or controlling one or more diseases or conditions selected from the group consisting of Type 2 diabetes, inadequate glucose tolerance, insulin resistance, obesity, hyperlipidemia, hypertriglyceridemia, hypercholesterolemia, low HDL levels, atherosclerosis, vascular restenosis, inflammatory bowel disease, pancreatitis, and dyslipidemia, said method comprising the administration of an effective amount of the compound of claim 1.

* * * * *